(12) United States Patent
Lam et al.

(10) Patent No.: US 9,585,651 B2
(45) Date of Patent: Mar. 7, 2017

(54) METHODS AND APPARATUS FOR SECURING AND DEPLOYING TISSUE ANCHORS

(75) Inventors: Cang C. Lam, Irvine, CA (US); Richard C. Ewers, Fullerton, CA (US); Robert A. Vaughan, Laguna Niguel, CA (US); Vahid Saadat, Saratoga, CA (US)

(73) Assignee: USGI Medical, Inc., San Clemente, CA (US)

( * ) Notice: Subject to any disclaimer, the term of this patent is extended or adjusted under 35 U.S.C. 154(b) by 2589 days.

(21) Appl. No.: 11/139,920

(22) Filed: May 26, 2005

(65) Prior Publication Data

US 2006/0271073 A1 Nov. 30, 2006

(51) Int. Cl.
*A61B 17/04* (2006.01)
*A61B 17/29* (2006.01)
(Continued)

(52) U.S. Cl.
CPC ...... *A61B 17/0482* (2013.01); *A61B 17/0401* (2013.01); *A61B 17/0469* (2013.01); *A61B 17/0487* (2013.01); *A61B 17/29* (2013.01); *A61B 2017/003* (2013.01); *A61B 2017/00349* (2013.01); *A61B 2017/00827* (2013.01); *A61B 2017/00867* (2013.01);
(Continued)

(58) Field of Classification Search
CPC . A61B 17/0401; A61B 17/0469; A61B 17/29; A61B 2017/00349; A61B 2017/0419; A61B 2017/0458; A61B 2017/06052; A61B 2017/2927; A61B 2017/00827; A61B 17/0487

USPC .......................................... 606/139, 144–150
See application file for complete search history.

(56) References Cited

U.S. PATENT DOCUMENTS 2,201,610 A 5/1940 Dawson
2,413,142 A 12/1946 Jones et al.
(Continued)

FOREIGN PATENT DOCUMENTS

WO WO 01/89393 A1 11/2001
WO WO 03/053253 A1 7/2003

OTHER PUBLICATIONS

AngioLINK, The Expanding Vascular Staple [brochure], Nov. 2004, 1 page total.
(Continued)

*Primary Examiner* — Gregory Anderson
(74) *Attorney, Agent, or Firm* — Kenneth H. Ohriner; Perkins Coie LLP

(57) ABSTRACT

Methods and apparatus for securing and deploying tissue anchors are described herein. A tissue manipulation assembly is pivotably coupled to the distal end of a tubular member. A reconfigurable launch tube is also pivotably coupled to the tissue manipulation assembly, which may be advanced through a shape-lockable endoscopic device, a conventional endoscope, or directly by itself into a patient. A second tool can be used in combination with the tissue manipulation assembly to engage tissue and manipulate the tissue in conjunction with the tissue manipulation assembly. A deployment assembly is provided for securing engaged tissue via one or more tissue anchors, the deployment assembly also being configured to disengage the anchors endoluminally or laparoscopically.

10 Claims, 21 Drawing Sheets

(51) Int. Cl.
*A61B 17/00* (2006.01)
*A61B 17/06* (2006.01)

(52) U.S. Cl.
CPC .............. *A61B 2017/0419* (2013.01); *A61B 2017/0458* (2013.01); *A61B 2017/0464* (2013.01); *A61B 2017/0496* (2013.01); *A61B 2017/06052* (2013.01); *A61B 2017/2927* (2013.01)

(56) References Cited

U.S. PATENT DOCUMENTS

| | | |
|---|---|---|
| 3,143,916 A | 8/1964 | Rice |
| 3,150,379 A | 9/1964 | Brown |
| 3,166,072 A | 1/1965 | Sullivan |
| 3,316,796 A | 5/1967 | Young |
| 3,410,269 A | 11/1968 | Hovick |
| 3,494,006 A | 2/1970 | Brumlik |
| 2,506,007 A | 4/1970 | Henkin |
| 3,546,961 A | 12/1970 | Marton |
| 3,551,987 A | 1/1971 | Wilkinson |
| 3,646,615 A | 3/1972 | Ness |
| 3,664,345 A | 5/1972 | Dabbs et al. |
| 3,753,438 A | 8/1973 | Wood et al. |
| 3,867,944 A | 2/1975 | Samuels |
| 3,874,388 A | 4/1975 | King et al. |
| 3,910,281 A | 10/1975 | Kletschka et al. |
| 3,915,157 A | 10/1975 | Mitsui |
| 3,976,079 A | 8/1976 | Samuels et al. |
| 4,006,747 A | 2/1977 | Kronenthal et al. |
| 4,007,743 A | 2/1977 | Blake |
| 4,060,089 A | 11/1977 | Noiles |
| 4,069,825 A | 1/1978 | Akiyama |
| 4,222,380 A | 9/1980 | Terayama |
| 4,235,238 A * | 11/1980 | Ogiu et al. ................ 606/145 |
| 4,245,624 A | 1/1981 | Komiya |
| 4,367,746 A | 1/1983 | Derechinsky |
| 4,414,720 A | 11/1983 | Crooms |
| 4,462,402 A | 7/1984 | Burgio et al. |
| 4,494,531 A | 1/1985 | Gianturco |
| 4,532,926 A | 8/1985 | O'Holla |
| 4,534,350 A | 8/1985 | Golden et al. |
| 4,548,202 A | 10/1985 | Duncan |
| 4,586,503 A | 5/1986 | Kirsch et al. |
| 4,592,339 A | 6/1986 | Kuzmak et al. |
| 4,592,356 A | 6/1986 | Gutierrez |
| 4,595,007 A | 6/1986 | Mericle |
| 4,610,250 A | 9/1986 | Green |
| 4,669,473 A | 6/1987 | Richards et al. |
| 4,705,040 A | 11/1987 | Mueller et al. |
| 4,711,002 A | 12/1987 | Kreeger |
| 4,724,840 A | 2/1988 | McVay et al. |
| 4,750,492 A | 6/1988 | Jacobs |
| 4,763,669 A | 8/1988 | Jaeger |
| 4,765,335 A | 8/1988 | Schmidt et al. |
| 4,769,874 A | 9/1988 | Tracy |
| 4,828,439 A | 5/1989 | Giannuzzi |
| 4,832,055 A | 5/1989 | Palestrant |
| 4,841,888 A | 6/1989 | Mills et al. |
| 4,872,579 A | 10/1989 | Palmer |
| 4,873,976 A | 10/1989 | Schreiber |
| 4,878,270 A | 11/1989 | Westerkamp |
| 4,881,302 A | 11/1989 | Lee |
| 4,890,615 A | 1/1990 | Caspari et al. |
| 4,923,461 A | 5/1990 | Caspari et al. |
| 4,929,240 A | 5/1990 | Kirsch et al. |
| 4,932,394 A | 6/1990 | Nanaumi |
| 4,949,927 A | 8/1990 | Madocks et al. |
| 4,957,498 A | 9/1990 | Caspari et al. |
| 5,032,127 A | 7/1991 | Frazee et al. |
| 5,035,692 A | 7/1991 | Lyon et al. |
| 5,037,433 A | 8/1991 | Wilk et al. |
| 5,041,129 A | 8/1991 | Hayhurst et al. |
| 5,059,201 A | 10/1991 | Asnis |
| 5,088,979 A | 2/1992 | Filipi et al. |
| 5,100,418 A | 3/1992 | Yoon et al. |
| 5,108,420 A | 4/1992 | Marks |
| 5,122,136 A | 6/1992 | Guglielmi et al. |
| 5,123,914 A | 6/1992 | Cope |
| RE34,021 E | 8/1992 | Mueller et al. |
| 5,176,691 A | 1/1993 | Pierce |
| 5,201,746 A | 4/1993 | Shichman |
| 5,203,864 A | 4/1993 | Phillips |
| 5,217,471 A | 6/1993 | Burkhart |
| 5,217,473 A | 6/1993 | Yoon |
| 5,222,508 A | 6/1993 | Contarini |
| 5,222,961 A | 6/1993 | Nakao et al. |
| 5,222,963 A | 6/1993 | Brinkerhoff et al. |
| 5,224,946 A | 7/1993 | Hayhurst et al. |
| 5,234,430 A | 8/1993 | Huebner |
| 5,234,445 A | 8/1993 | Walker et al. |
| 5,241,968 A | 9/1993 | Slater |
| 5,250,053 A | 10/1993 | Snyder |
| 5,254,126 A | 10/1993 | Filipi et al. |
| 5,258,015 A | 11/1993 | Li et al. |
| 5,258,016 A | 11/1993 | DiPoto et al. |
| 5,261,916 A | 11/1993 | Engelson |
| 5,268,001 A | 12/1993 | Nicholson et al. |
| 5,269,809 A | 12/1993 | Hayhurst et al. |
| 5,282,827 A | 2/1994 | Kensey et al. |
| 5,284,488 A | 2/1994 | Sideris |
| 5,290,296 A | 3/1994 | Phillips |
| 5,304,184 A | 4/1994 | Hathaway et al. |
| 5,304,195 A | 4/1994 | Twyford et al. |
| 5,304,204 A | 4/1994 | Bregen |
| 5,316,543 A | 5/1994 | Eberbach |
| 5,318,589 A | 6/1994 | Lichtman |
| 5,327,914 A | 7/1994 | Shlain |
| 5,330,503 A | 7/1994 | Yoon |
| 5,334,217 A | 8/1994 | Das |
| 5,342,376 A | 8/1994 | Ruff |
| 5,345,949 A | 9/1994 | Shlain |
| 5,350,399 A | 9/1994 | Erlebacher et al. |
| 5,354,298 A | 10/1994 | Lee et al. |
| 5,366,459 A | 11/1994 | Yoon |
| 5,366,479 A | 11/1994 | McGarry et al. |
| 5,370,661 A | 12/1994 | Branch |
| 5,372,146 A | 12/1994 | Branch |
| 5,372,604 A | 12/1994 | Trott |
| 5,374,275 A | 12/1994 | Bradley et al. |
| 5,380,334 A | 1/1995 | Torrie et al. |
| 5,382,231 A | 1/1995 | Shlain |
| 5,383,905 A | 1/1995 | Golds et al. |
| 5,395,030 A | 3/1995 | Kuramoto et al. |
| 5,403,326 A | 4/1995 | Harrison et al. |
| 5,403,329 A | 4/1995 | Hinchcliffe |
| 5,417,691 A | 5/1995 | Hayhurst |
| 5,417,699 A | 5/1995 | Klein et al. |
| 5,423,854 A | 6/1995 | Martin et al. |
| 5,425,744 A | 6/1995 | Fagan et al. |
| 5,429,598 A | 7/1995 | Waxman et al. |
| 5,431,666 A | 7/1995 | Sauer et al. |
| 5,433,721 A | 7/1995 | Hooven et al. |
| 5,433,727 A | 7/1995 | Sideris |
| 5,437,680 A | 8/1995 | Yoon |
| 5,437,681 A | 8/1995 | Meade et al. |
| 5,445,167 A | 8/1995 | Yoon et al. |
| 5,458,609 A | 10/1995 | Gordon et al. |
| 5,462,560 A | 10/1995 | Stevens |
| 5,462,561 A | 10/1995 | Voda |
| 5,465,894 A | 11/1995 | Clark et al. |
| 5,470,337 A | 11/1995 | Moss |
| 5,470,338 A | 11/1995 | Whitfield et al. |
| 5,476,470 A | 12/1995 | Fitzgibbons |
| 5,478,354 A | 12/1995 | Tovey et al. |
| 5,480,405 A | 1/1996 | Yoon |
| 5,496,332 A * | 3/1996 | Sierra ................ A61B 17/0057 606/139 |
| 5,496,334 A | 3/1996 | Klundt et al. |
| 5,499,991 A | 3/1996 | Garman et al. |
| 5,501,691 A | 3/1996 | Goldrath |
| 5,507,811 A | 4/1996 | Koike et al. |
| 5,520,691 A | 5/1996 | Branch |
| 5,520,701 A | 5/1996 | Lerch |

(56) References Cited

U.S. PATENT DOCUMENTS

| | | |
|---|---|---|
| 5,522,843 A | 6/1996 | Zang |
| 5,527,320 A | 6/1996 | Carruthers et al. |
| 5,527,321 A | 6/1996 | Hinchliffe |
| 5,527,322 A | 6/1996 | Klein et al. |
| 5,527,342 A | 6/1996 | Pietrzak et al. |
| 5,531,759 A | 7/1996 | Kensey et al. |
| 5,531,788 A | 7/1996 | Dibie et al. |
| 5,535,759 A | 7/1996 | Wilk |
| 5,540,704 A | 7/1996 | Gordon et al. |
| 5,549,618 A | 8/1996 | Fleenor et al. |
| 5,549,621 A | 8/1996 | Bessler et al. |
| 5,562,684 A | 10/1996 | Kammerer |
| 5,562,686 A | 10/1996 | Sauer et al. |
| 5,562,688 A | 10/1996 | Riza |
| 5,569,274 A | 10/1996 | Rapacki et al. |
| 5,569,306 A | 10/1996 | Thal |
| 5,571,116 A | 11/1996 | Bolanos et al. |
| 5,571,119 A | 11/1996 | Atala |
| 5,573,540 A | 11/1996 | Yoon |
| 5,573,548 A | 11/1996 | Nazre et al. |
| 5,575,801 A | 11/1996 | Habermeyer et al. |
| 5,578,045 A | 11/1996 | Das |
| 5,582,616 A | 12/1996 | Bolduc et al. |
| 5,582,617 A | 12/1996 | Klieman et al. |
| 5,584,835 A | 12/1996 | Greenfield |
| 5,584,859 A | 12/1996 | Brotz |
| 5,601,557 A | 2/1997 | Hayhurst |
| 5,603,718 A | 2/1997 | Xu |
| 5,613,974 A | 3/1997 | Andreas et al. |
| 5,613,975 A | 3/1997 | Christy |
| 5,626,588 A | 5/1997 | Sauer et al. |
| 5,626,614 A | 5/1997 | Hart |
| 5,630,540 A | 5/1997 | Blewett |
| 5,632,752 A | 5/1997 | Buelna |
| 5,643,274 A | 7/1997 | Sander et al. |
| 5,643,289 A | 7/1997 | Sauer et al. |
| 5,643,295 A | 7/1997 | Yoon |
| 5,643,317 A | 7/1997 | Pavcnik et al. |
| 5,643,320 A | 7/1997 | Lower et al. |
| 5,658,312 A | 8/1997 | Green et al. |
| 5,658,313 A | 8/1997 | Thal |
| 5,662,654 A | 9/1997 | Thompson |
| 5,662,662 A | 9/1997 | Bishop et al. |
| 5,662,663 A | 9/1997 | Shallman |
| 5,665,109 A | 9/1997 | Yoon |
| 5,665,112 A | 9/1997 | Thal |
| 5,667,513 A | 9/1997 | Torrie et al. |
| 5,669,935 A | 9/1997 | Rosenman et al. |
| 5,679,005 A | 10/1997 | Einstein |
| 5,683,417 A | 11/1997 | Cooper |
| 5,683,419 A | 11/1997 | Thal |
| 5,690,655 A | 11/1997 | Hart et al. |
| 5,693,060 A | 12/1997 | Martin |
| 5,700,273 A | 12/1997 | Buelna et al. |
| 5,702,397 A | 12/1997 | Goble et al. |
| 5,702,421 A | 12/1997 | Schneidt |
| 5,707,394 A | 1/1998 | Miller et al. |
| 5,709,708 A | 1/1998 | Thal |
| 5,713,903 A | 2/1998 | Sander et al. |
| 5,720,765 A | 2/1998 | Thal |
| 5,724,978 A | 3/1998 | Tenhoff |
| 5,725,552 A | 3/1998 | Kotula et al. |
| 5,732,707 A | 3/1998 | Widder et al. |
| 5,741,297 A | 4/1998 | Simon |
| 5,746,752 A | 5/1998 | Burkhart |
| 5,746,755 A | 5/1998 | Wood et al. |
| 5,749,893 A | 5/1998 | Vidal et al. |
| 5,752,963 A | 5/1998 | Allard et al. |
| 5,766,189 A | 6/1998 | Matsuno |
| 5,766,196 A | 6/1998 | Griffiths |
| 5,776,150 A | 7/1998 | Nolan et al. |
| 5,779,719 A | 7/1998 | Klein et al. |
| 5,782,859 A | 7/1998 | Nicholas et al. |
| 5,782,865 A | 7/1998 | Grotz |
| 5,787,897 A | 8/1998 | Kieturakis |
| 5,792,152 A | 8/1998 | Klein et al. |
| 5,792,153 A | 8/1998 | Swain et al. |
| 5,797,927 A | 8/1998 | Yoon |
| 5,797,929 A | 8/1998 | Andreas et al. |
| 5,797,960 A | 8/1998 | Stevens et al. |
| 5,810,848 A | 9/1998 | Hayhurst |
| 5,810,849 A | 9/1998 | Kontos |
| 5,810,851 A | 9/1998 | Yoon |
| 5,810,853 A | 9/1998 | Yoon |
| 5,810,879 A | 9/1998 | de Guillebon |
| 5,814,070 A | 9/1998 | Borzone et al. |
| 5,817,064 A | 10/1998 | DeMarco et al. |
| 5,817,107 A | 10/1998 | Schaller |
| 5,817,110 A | 10/1998 | Kronner |
| 5,823,940 A | 10/1998 | Newman |
| 5,823,956 A | 10/1998 | Roth et al. |
| 5,824,011 A | 10/1998 | Stone et al. |
| 5,827,298 A | 10/1998 | Hart et al. |
| 5,829,447 A | 11/1998 | Stevens et al. |
| 5,836,955 A | 11/1998 | Buelna et al. |
| 5,840,078 A | 11/1998 | Yerys |
| 5,843,084 A | 12/1998 | Hart et al. |
| 5,843,126 A | 12/1998 | Jameel |
| 5,846,261 A | 12/1998 | Kotula et al. |
| 5,853,422 A | 12/1998 | Huebsch et al. |
| 5,855,614 A | 1/1999 | Stevens et al. |
| 5,860,914 A | 1/1999 | Chiba et al. |
| 5,860,991 A | 1/1999 | Klein et al. |
| 5,861,003 A | 1/1999 | Latson et al. |
| 5,865,791 A | 2/1999 | Whayne et al. |
| 5,868,762 A | 2/1999 | Cragg et al. |
| 5,879,371 A | 3/1999 | Gardiner et al. |
| 5,887,594 A | 3/1999 | LoCicero |
| 5,888,247 A | 3/1999 | Benetti |
| 5,891,168 A | 4/1999 | Thal |
| 5,893,856 A | 4/1999 | Jacob et al. |
| 5,895,404 A | 4/1999 | Ruiz |
| 5,897,562 A | 4/1999 | Bolanos et al. |
| 5,899,914 A | 5/1999 | Zirps et al. |
| 5,899,920 A | 5/1999 | DeSatnick et al. |
| 5,901,895 A | 5/1999 | Heaton et al. |
| 5,902,321 A | 5/1999 | Caspari et al. |
| 5,916,224 A | 6/1999 | Esplin |
| 5,925,059 A | 7/1999 | Palermo et al. |
| 5,928,260 A | 7/1999 | Chin et al. |
| 5,928,264 A | 7/1999 | Sugarbaker et al. |
| 5,944,738 A | 8/1999 | Amplatz et al. |
| 5,947,983 A | 9/1999 | Solar et al. |
| 5,947,997 A | 9/1999 | Pavcnik et al. |
| 5,948,001 A | 9/1999 | Larsen |
| 5,954,731 A | 9/1999 | Yoon |
| 5,954,732 A | 9/1999 | Hart et al. |
| 5,954,733 A | 9/1999 | Yoon |
| 5,961,440 A | 10/1999 | Schweich et al. |
| 5,964,765 A | 10/1999 | Fenton et al. |
| 5,964,782 A | 10/1999 | Lafontaine et al. |
| 5,964,783 A | 10/1999 | Grafton et al. |
| 5,976,073 A | 11/1999 | Ouchi |
| 5,976,127 A | 11/1999 | Lax |
| 5,976,158 A | 11/1999 | Adams et al. |
| 5,976,159 A | 11/1999 | Bolduc et al. |
| 5,980,558 A | 11/1999 | Wiley |
| 5,984,933 A | 11/1999 | Yoon |
| 5,993,476 A | 11/1999 | Groiso |
| 6,013,083 A | 1/2000 | Bennett |
| 6,017,358 A | 1/2000 | Yoon et al. |
| 6,027,523 A | 2/2000 | Schmieding |
| 6,033,430 A | 3/2000 | Bonutti |
| 6,036,699 A | 3/2000 | Andreas et al. |
| 6,042,155 A | 3/2000 | Lockwood |
| 6,045,497 A | 4/2000 | Schweich et al. |
| 6,045,551 A | 4/2000 | Bonutti |
| 6,045,573 A | 4/2000 | Wenstrom et al. |
| 6,050,936 A | 4/2000 | Schweich et al. |
| 6,053,935 A | 4/2000 | Brenneman et al. |
| 6,059,715 A | 5/2000 | Schweich et al. |
| 6,059,719 A | 5/2000 | Yamamoto et al. |
| 6,074,401 A | 6/2000 | Gardiner et al. |
| 6,077,214 A | 6/2000 | Mortier et al. |

(56) References Cited

U.S. PATENT DOCUMENTS

| | | |
|---|---|---|
| 6,077,281 A | 6/2000 | Das |
| 6,077,291 A | 6/2000 | Das |
| 6,079,414 A | 6/2000 | Roth |
| 6,086,600 A | 7/2000 | Kortenbach |
| 6,086,601 A | 7/2000 | Yoon |
| 6,099,553 A | 8/2000 | Hart et al. |
| 6,110,183 A | 8/2000 | Cope |
| 6,113,609 A | 9/2000 | Adams |
| 6,113,611 A | 9/2000 | Allen et al. |
| 6,119,913 A | 9/2000 | Adams et al. |
| 6,149,658 A | 11/2000 | Gardiner et al. |
| 6,152,935 A | 11/2000 | Kammerer et al. |
| 6,152,946 A | 11/2000 | Broome et al. |
| 6,159,146 A | 12/2000 | El Gazayerli |
| 6,162,168 A | 12/2000 | Schweich et al. |
| 6,165,119 A | 12/2000 | Schweich et al. |
| 6,165,120 A | 12/2000 | Schweich et al. |
| 6,167,889 B1 | 1/2001 | Benetti |
| 6,171,320 B1 | 1/2001 | Monassevitch |
| 6,174,323 B1 | 1/2001 | Biggs et al. |
| 6,179,195 B1 | 1/2001 | Adams et al. |
| 6,183,411 B1 | 2/2001 | Mortier et al. |
| 6,190,401 B1 | 2/2001 | Green et al. |
| RE37,117 E | 3/2001 | Palermo |
| 6,197,022 B1 | 3/2001 | Baker |
| 6,214,007 B1 | 4/2001 | Anderson |
| 6,221,084 B1 | 4/2001 | Fleenor |
| 6,231,561 B1 | 5/2001 | Frazier et al. |
| 6,241,748 B1 | 6/2001 | Adams |
| 6,245,079 B1 | 6/2001 | Nobles et al. |
| 6,260,552 B1 | 7/2001 | Mortier et al. |
| 6,261,222 B1 | 7/2001 | Schweich et al. |
| 6,264,602 B1 | 7/2001 | Mortier et al. |
| 6,270,515 B1 | 8/2001 | Linden et al. |
| 6,283,973 B1 | 9/2001 | Hubbard et al. |
| 6,287,317 B1 | 9/2001 | Makower et al. |
| 6,290,674 B1 | 9/2001 | Roue et al. |
| 6,293,956 B1 | 9/2001 | Crainich et al. |
| 6,296,656 B1 | 10/2001 | Bolduc et al. |
| 6,306,159 B1 | 10/2001 | Schwartz et al. |
| 6,306,163 B1 | 10/2001 | Fitz |
| 6,312,437 B1 | 11/2001 | Kortenbach |
| 6,315,789 B1 | 11/2001 | Cragg |
| 6,322,563 B1 | 11/2001 | Cummings et al. |
| 6,322,580 B1 | 11/2001 | Kanner |
| 6,328,727 B1 | 12/2001 | Frazier et al. |
| 6,332,468 B1 | 12/2001 | Benetti |
| 6,332,863 B1 | 12/2001 | Schweich et al. |
| 6,332,864 B1 | 12/2001 | Schweich et al. |
| 6,332,893 B1 | 12/2001 | Mortier et al. |
| 6,336,940 B1 | 1/2002 | Graf et al. |
| 6,346,074 B1 | 2/2002 | Roth |
| 6,348,064 B1 | 2/2002 | Kanner |
| 6,352,503 B1 | 3/2002 | Matsui et al. |
| 6,355,052 B1 | 3/2002 | Neuss et al. |
| 6,358,197 B1 | 3/2002 | Silverman et al. |
| 6,363,938 B2 | 4/2002 | Saadat et al. |
| 6,368,338 B1 | 4/2002 | Konya et al. |
| 6,368,339 B1 | 4/2002 | Amplatz |
| 6,371,971 B1 | 4/2002 | Tsugita et al. |
| 6,375,668 B1 | 4/2002 | Gifford et al. |
| 6,387,104 B1 | 5/2002 | Pugsley et al. |
| 6,394,949 B1 | 5/2002 | Crowley et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| H2037 H | 7/2002 | Yates et al. |
| 6,423,087 B1 | 7/2002 | Sawada |
| 6,425,911 B1 | 7/2002 | Akerfeldt et al. |
| 6,447,533 B1 | 9/2002 | Adams |
| 6,491,714 B1 | 12/2002 | Bennett |
| 6,494,888 B1 | 12/2002 | Laufer et al. |
| 6,506,196 B1 | 1/2003 | Laufer |
| 6,508,828 B1 | 1/2003 | Akerfeldt et al. |
| 6,517,552 B1 | 2/2003 | Nord et al. |
| 6,533,796 B1 | 3/2003 | Sauer et al. |
| 6,537,285 B1 | 3/2003 | Hatasaka et al. |
| 6,551,315 B2 | 4/2003 | Kortenbach et al. |
| 6,554,845 B1 | 4/2003 | Fleenor et al. |
| 6,558,400 B2 | 5/2003 | Deem et al. |
| 6,569,085 B2 | 5/2003 | Kortenbach et al. |
| 6,572,629 B2 | 6/2003 | Kalloo et al. |
| 6,582,453 B1 | 6/2003 | Tran et al. |
| 6,589,208 B2 | 7/2003 | Ewers et al. |
| 6,592,596 B1 | 7/2003 | Geitz |
| 6,595,984 B1 | 7/2003 | DeGuillebon |
| 6,641,592 B1 | 11/2003 | Sauer et al. |
| 6,656,194 B1 | 12/2003 | Gannoe et al. |
| 6,663,639 B1 | 12/2003 | Laufer et al. |
| 6,669,713 B2 | 12/2003 | Adams |
| 6,689,051 B2 | 2/2004 | Nakada et al. |
| 6,692,506 B1 | 2/2004 | Ory et al. |
| 6,695,764 B2 | 2/2004 | Silverman et al. |
| 6,699,233 B2 | 3/2004 | Slanda et al. |
| 6,716,232 B1 | 4/2004 | Vidal et al. |
| 6,719,763 B2 | 4/2004 | Chung et al. |
| 6,719,764 B1 | 4/2004 | Gellman et al. |
| 6,736,828 B1 | 5/2004 | Adams et al. |
| 6,743,240 B2 | 6/2004 | Smith et al. |
| 6,746,460 B2 | 6/2004 | Gannoe et al. |
| 6,746,472 B2 | 6/2004 | Frazier et al. |
| 6,755,843 B2 | 6/2004 | Chung et al. |
| 6,761,685 B2 | 7/2004 | Adams et al. |
| 6,773,440 B2 | 8/2004 | Gannoe et al. |
| 6,773,441 B1 | 8/2004 | Laufer et al. |
| 6,821,285 B2 | 11/2004 | Laufer et al. |
| 6,835,199 B2 | 12/2004 | McGuckin et al. |
| 6,932,834 B2 | 8/2005 | Lizardi et al. |
| 6,955,643 B2 | 10/2005 | Gellman et al. |
| 6,986,781 B2 | 1/2006 | Smith |
| 7,033,379 B2 | 4/2006 | Peterson |
| 7,048,754 B2 | 5/2006 | Martin et al. |
| 7,090,690 B2 | 8/2006 | Foerster et al. |
| 7,112,208 B2 | 9/2006 | Morris et al. |
| 7,160,312 B2 | 1/2007 | Saadat |
| 7,316,703 B2 | 1/2008 | Suzuki |
| 7,347,863 B2 | 3/2008 | Rothe et al. |
| 7,416,554 B2 * | 8/2008 | Lam et al. .................. 606/153 |
| 7,618,426 B2 | 11/2009 | Ewers et al. |
| 7,736,374 B2 | 6/2010 | Vaughan et al. |
| 2001/0016675 A1 | 8/2001 | Mortier et al. |
| 2001/0025171 A1 | 9/2001 | Mortier et al. |
| 2001/0025185 A1 | 9/2001 | Laufer et al. |
| 2001/0049509 A1 | 12/2001 | Sekine et al. |
| 2001/0051815 A1 | 12/2001 | Esplin |
| 2001/0051816 A1 | 12/2001 | Enzerink et al. |
| 2001/0056282 A1 | 12/2001 | Sonnenschein et al. |
| 2002/0010490 A1 | 1/2002 | Schaller et al. |
| 2002/0013570 A1 | 1/2002 | Ruegg et al. |
| 2002/0013608 A1 | 1/2002 | ElAttrache et al. |
| 2002/0019649 A1 | 2/2002 | Sikora et al. |
| 2002/0022851 A1 | 2/2002 | Kalloo et al. |
| 2002/0029080 A1 | 3/2002 | Mortier et al. |
| 2002/0040226 A1 | 4/2002 | Laufer et al. |
| 2002/0049458 A1 | 4/2002 | Singhatat |
| 2002/0055757 A1 | 5/2002 | Torre et al. |
| 2002/0058855 A1 | 5/2002 | Schweich et al. |
| 2002/0065534 A1 | 5/2002 | Hermann et al. |
| 2002/0068849 A1 | 6/2002 | Schweich et al. |
| 2002/0068945 A1 | 6/2002 | Sixto et al. |
| 2002/0072761 A1 | 6/2002 | Abrams et al. |
| 2002/0077524 A1 | 6/2002 | Schweich et al. |
| 2002/0078967 A1 | 6/2002 | Sixto et al. |
| 2002/0082621 A1 | 6/2002 | Schurr et al. |
| 2002/0082622 A1 | 6/2002 | Kane |
| 2002/0087049 A1 | 7/2002 | Brock et al. |
| 2002/0106597 A1 | 8/2002 | Grando et al. |
| 2002/0107530 A1 | 8/2002 | Sauer et al. |
| 2002/0111647 A1 | 8/2002 | Khairkhahan et al. |
| 2002/0116012 A1 | 8/2002 | May et al. |
| 2002/0151921 A1 | 10/2002 | Kanner et al. |
| 2002/0156344 A1 | 10/2002 | Pasricha et al. |
| 2002/0161281 A1 | 10/2002 | Jaffe et al. |
| 2002/0161395 A1 | 10/2002 | Douk et al. |

(56) References Cited

U.S. PATENT DOCUMENTS

| | | |
|---|---|---|
| 2002/0183765 A1 | 12/2002 | Adams |
| 2002/0183768 A1 | 12/2002 | Deem et al. |
| 2002/0188170 A1 | 12/2002 | Santamore et al. |
| 2002/0193816 A1 | 12/2002 | Laufer et al. |
| 2002/0198537 A1 | 12/2002 | Smith et al. |
| 2003/0009085 A1 | 1/2003 | Arai et al. |
| 2003/0055442 A1 | 3/2003 | Laufer et al. |
| 2003/0065359 A1 | 4/2003 | Weller et al. |
| 2003/0069593 A1 | 4/2003 | Tremulis et al. |
| 2003/0109892 A1 | 6/2003 | Deem et al. |
| 2003/0109900 A1 | 6/2003 | Martinek |
| 2003/0130561 A1 | 7/2003 | Suzuki et al. |
| 2003/0139752 A1 | 7/2003 | Pasricha et al. |
| 2003/0158582 A1 | 8/2003 | Bonutti et al. |
| 2003/0167062 A1 | 9/2003 | Gambale et al. |
| 2003/0171651 A1 | 9/2003 | Page et al. |
| 2003/0171760 A1 | 9/2003 | Gambale |
| 2003/0176890 A1 | 9/2003 | Buckman et al. |
| 2003/0181924 A1 | 9/2003 | Yamamoto et al. |
| 2003/0204205 A1 | 10/2003 | Sauer et al. |
| 2003/0208209 A1 | 11/2003 | Gambale et al. |
| 2003/0216613 A1 | 11/2003 | Suzuki et al. |
| 2003/0225312 A1 | 12/2003 | Suzuki et al. |
| 2003/0229296 A1 | 12/2003 | Ishikawa et al. |
| 2003/0236535 A1 * | 12/2003 | Onuki et al. ............... 606/144 |
| 2003/0236536 A1 | 12/2003 | Grigoryants et al. |
| 2004/0010271 A1 | 1/2004 | Kortenbach |
| 2004/0030347 A1 | 2/2004 | Gannoe et al. |
| 2004/0049095 A1 | 3/2004 | Goto et al. |
| 2004/0059346 A1 | 3/2004 | Adams et al. |
| 2004/0073089 A1 | 4/2004 | Nozue |
| 2004/0082963 A1 | 4/2004 | Gannoe et al. |
| 2004/0088008 A1 | 5/2004 | Gannoe et al. |
| 2004/0092974 A1 | 5/2004 | Gannoe et al. |
| 2004/0093091 A1 | 5/2004 | Gannoe et al. |
| 2004/0116949 A1 | 6/2004 | Ewers et al. |
| 2004/0122452 A1 | 6/2004 | Deem et al. |
| 2004/0122453 A1 | 6/2004 | Deem et al. |
| 2004/0122456 A1 | 6/2004 | Saadat et al. |
| 2004/0122473 A1 | 6/2004 | Ewers et al. |
| 2004/0122474 A1 | 6/2004 | Gellman et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0167546 A1 | 8/2004 | Saadat et al. |
| 2004/0176784 A1 | 9/2004 | Okada |
| 2004/0193117 A1 | 9/2004 | Laufer et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2004/0215216 A1 | 10/2004 | Gannoe et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0249362 A1 | 12/2004 | Levine et al. |
| 2004/0249367 A1 | 12/2004 | Saadat et al. |
| 2004/0249392 A1 | 12/2004 | Mikkaichi et al. |
| 2004/0249395 A1 | 12/2004 | Mikkaichi et al. |
| 2004/0260317 A1 | 12/2004 | Bloom et al. |
| 2004/0267306 A1 | 12/2004 | Blaeser et al. |
| 2005/0033320 A1 | 2/2005 | McGuckin et al. |
| 2005/0033328 A1 | 2/2005 | Laufer et al. |
| 2005/0033354 A1 | 2/2005 | Montalvo et al. |
| 2005/0043758 A1 | 2/2005 | Golden et al. |
| 2005/0049617 A1 | 3/2005 | Chatlynne et al. |
| 2005/0065397 A1 | 3/2005 | Saadat et al. |
| 2005/0065401 A1 | 3/2005 | Saadat et al. |
| 2005/0065536 A1 | 3/2005 | Ewers et al. |
| 2005/0075653 A1 | 4/2005 | Saadat et al. |
| 2005/0075654 A1 | 4/2005 | Kelleher |
| 2005/0113640 A1 | 5/2005 | Saadat et al. |
| 2005/0119671 A1 | 6/2005 | Reydel et al. |
| 2005/0125075 A1 | 6/2005 | Meade et al. |
| 2005/0149115 A1 | 7/2005 | Roue et al. |
| 2005/0192629 A1 | 9/2005 | Saadat et al. |
| 2005/0203488 A1 | 9/2005 | Michlitsch et al. |
| 2005/0203489 A1 | 9/2005 | Saadat et al. |
| 2005/0203500 A1 | 9/2005 | Saadat et al. |
| 2005/0216040 A1 | 9/2005 | Gertner et al. |
| 2005/0234294 A1 | 10/2005 | Saadat et al. |
| 2005/0234296 A1 | 10/2005 | Saadat et al. |
| 2005/0234512 A1 | 10/2005 | Nakao |
| 2005/0245932 A1 | 11/2005 | Fanton et al. |
| 2005/0245945 A1 | 11/2005 | Ewers et al. |
| 2005/0250980 A1 | 11/2005 | Swanstrom et al. |
| 2005/0250984 A1 | 11/2005 | Lam et al. |
| 2005/0250985 A1 | 11/2005 | Saadat et al. |
| 2005/0250986 A1 | 11/2005 | Rothe et al. |
| 2005/0250987 A1 | 11/2005 | Ewers et al. |
| 2005/0250988 A1 | 11/2005 | Ewers et al. |
| 2005/0251091 A1 | 11/2005 | Saadat et al. |
| 2005/0251157 A1 | 11/2005 | Saadat et al. |
| 2005/0251158 A1 | 11/2005 | Saadat et al. |
| 2005/0251159 A1 | 11/2005 | Ewers et al. |
| 2005/0251160 A1 | 11/2005 | Saadat et al. |
| 2005/0251161 A1 | 11/2005 | Saadat et al. |
| 2005/0251162 A1 | 11/2005 | Rothe et al. |
| 2005/0251165 A1 | 11/2005 | Vaughan et al. |
| 2005/0251166 A1 | 11/2005 | Vaughan et al. |
| 2005/0251176 A1 | 11/2005 | Swanstrom et al. |
| 2005/0251177 A1 | 11/2005 | Saadat et al. |
| 2005/0251189 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267523 A1 | 12/2005 | Devellian et al. |
| 2005/0272977 A1 | 12/2005 | Saadat et al. |
| 2005/0273135 A1 | 12/2005 | Chanduszko et al. |
| 2005/0277945 A1 | 12/2005 | Saadat et al. |
| 2005/0277966 A1 | 12/2005 | Ewers et al. |
| 2005/0277975 A1 | 12/2005 | Saadat et al. |
| 2005/0277981 A1 | 12/2005 | Maahs et al. |
| 2005/0277983 A1 | 12/2005 | Saadat et al. |
| 2006/0009789 A1 | 1/2006 | Gambale et al. |
| 2006/0020274 A1 | 1/2006 | Ewers et al. |
| 2006/0020276 A1 | 1/2006 | Saadat et al. |
| 2006/0030884 A1 * | 2/2006 | Yeung et al. ............... 606/232 |
| 2006/0100579 A1 | 5/2006 | Maahs et al. |
| 2006/0135971 A1 | 6/2006 | Swanstrom et al. |
| 2006/0157067 A1 | 7/2006 | Saadat et al. |
| 2006/0161185 A1 | 7/2006 | Saadat et al. |
| 2006/0178560 A1 | 8/2006 | Saadat et al. |
| 2006/0178562 A1 | 8/2006 | Saadat et al. |
| 2006/0178680 A1 * | 8/2006 | Nelson et al. ............... 606/139 |
| 2006/0183975 A1 | 8/2006 | Saadat et al. |
| 2006/0184161 A1 | 8/2006 | Maahs et al. |
| 2006/0189845 A1 | 8/2006 | Maahs et al. |
| 2006/0217762 A1 | 9/2006 | Maahs et al. |
| 2006/0237022 A1 | 10/2006 | Chen et al. |
| 2006/0237023 A1 | 10/2006 | Cox et al. |
| 2006/0258909 A1 | 11/2006 | Saadat et al. |
| 2006/0271073 A1 | 11/2006 | Lam et al. |
| 2006/0271074 A1 | 11/2006 | Ewers et al. |
| 2006/0271101 A1 | 11/2006 | Saadat et al. |
| 2007/0123840 A1 | 5/2007 | Cox |
| 2007/0142849 A1 | 6/2007 | Ewers et al. |

OTHER PUBLICATIONS

Bluett et al., "Experimental Evaluation of Staple Lines in Gastric Surgery," *Arch. Surg.*, vol. 122, Jul. 1987, pp. 772-776.

Brolin et al., "Experimental Evaluation of Techniques of Gastric Paritioning for Morbid Obesity," *Surgery, Gynecology & Obstetrics*, vol. 153, Dec. 1981, pp. 878-882.

Chuttani, Ram et al. "A Novel Endoscopic Full-Thickness Plicator for Treatment of DERD: An Animal Model Study," *Gastointestinal Endoscopy*, 2002, vol. 56, pp. 116-122.

(56) References Cited

OTHER PUBLICATIONS

Johnston et al., "The Magenstrasse and Mill Operation of Morbid Obesity," *Obesity Surgery* 13, 2003, pp. 10-16.
Microline, 5mm Reusable Graspers, [Brochure], date unknown, 1 page.
Okudaira et al., "The Healing and Tensile Strength of the Gastroplasty Staple Line," *The American Surgeon*, Oct. 1984, pp. 564-568.
Surgical Dynamics, Inc., The S D sorb Meniscal Stapler [brochure] (1997), 3 pages total.
Sutura, The Next Generation in Vascular Suturing Devices: Superstitch [brochure] 2004, 2 pages total.
File History for European Patent Application No. 05746261.6 filed May 6, 2005.
File History for European Patent Application No. 05800802.0 filed Sep. 22, 2005.
File History for European Patent Application No. 06787107.9 filed Jul. 11, 2006.
File History for PCT International Patent Application No. PCT/US2005/034311 filed Sep. 22, 2005.
File History for PCT International Patent Application No. PCT/US2006/007114 filed Feb. 28, 2006.
File History for PCT International Patent Application No. PCT/US2006/027157 filed Jul. 11, 2006.
File History for U.S. Appl. No. 10/840,950, filed May 7, 2004.
File History for U.S. Appl. No. 10/841,245, filed May 7, 2004.
File History for U.S. Appl. No. 10/841,411, filed May 7, 2004.
File History for U.S. Appl. No. 10/865,736, filed Jun. 9, 2004.
File History for U.S. Appl. No. 10/869,472, filed Jun. 15, 2004.
File History for U.S. Appl. No. 10/954,665, filed Sep. 29, 2004.
File History for U.S. Appl. No. 10/954,666, filed Sep. 29, 2004.
File History for U.S. Appl. No. 10/955,243, filed Sep. 30, 2004.
File History for U.S. Appl. No. 10/955,244, filed Sep. 30, 2004.
File History for U.S. Appl. No. 10/955,245, filed Sep. 29, 2004.
File History for U.S. Appl. No. 10/956,009, filed Sep. 29 2004.
File History for U.S. Appl. No. 11/036,366, filed Jan. 14, 2005.
File History for U.S. Appl. No 11/036,946, filed Jun. 24, 2008.
File History for U.S. Appl. No. 11/070,846, filed Mar. 1, 2005.
File History for U.S. Appl. No. 11/070,863, filed Mar. 1, 2005.
File History for U.S. Appl. No. 11/118,876, filed Apr. 28, 2005.
File History for U.S. Appl. No 11/179,082, filed Jul. 11, 2005.
File History for U.S. Appl. No. 11/238,543, filed Sep. 30, 2005.
File History for U.S. Appl. No. 11/404,423, filed Apr. 14, 2006.
File History for U.S. Appl. No. 11/412,261, filed Apr. 26, 2006.
File History for U.S. Appl. No. 11/951,188, filed Dec. 5, 2007.
File History for U.S. Appl. No. 12/054,297, filed Mar. 24, 2008.
File History for U.S. Appl. No. 12/107,701, filed Apr. 22, 2008.
File History for U.S. Appl. No. 12/552,255, filed Sep. 1, 2009.
File History for U.S. Appl. No. 12/579,295, filed Oct. 14, 2009.
File History for U.S. Appl. No. 12/724,348, filed Mar. 15, 2010.
File History for U.S. Appl. No. 12/815,335, filed Jun. 14, 2010.
PCT International Patent Application No. PCT/US2005/01765 filed May 6, 2005, International Preliminary Report on Patentability mailed Nov. 16, 2006.
PCT International Patent Application No. PCT/US2005/034117 filed Sep. 22, 2005, International Preliminary Report on Patentability mailed Apr. 12, 2007.
PCT International Patent Application No. PCT/US2005/034117 filed Sep. 22, 2005, International Search Report mailed Apr. 7, 2006.
PCT International Patent Application No. PCT/US2005/034685 filed Sep. 26, 2005, International Preliminary Report on Patentability mailed Mar. 5, 2009.
PCT International Patent Application No. PCT/US2005/034685 filed Sep. 26, 2005, International Search Report mailed May 22, 2008.

\* cited by examiner

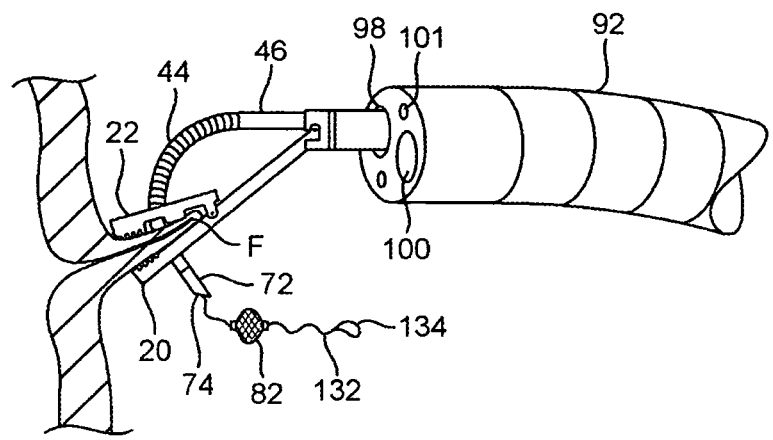
FIG. 8D
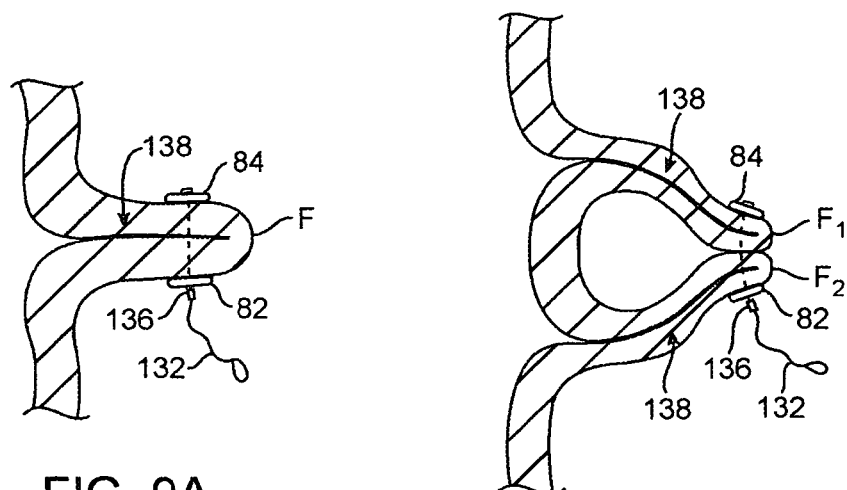
FIG. 9A
FIG. 9B

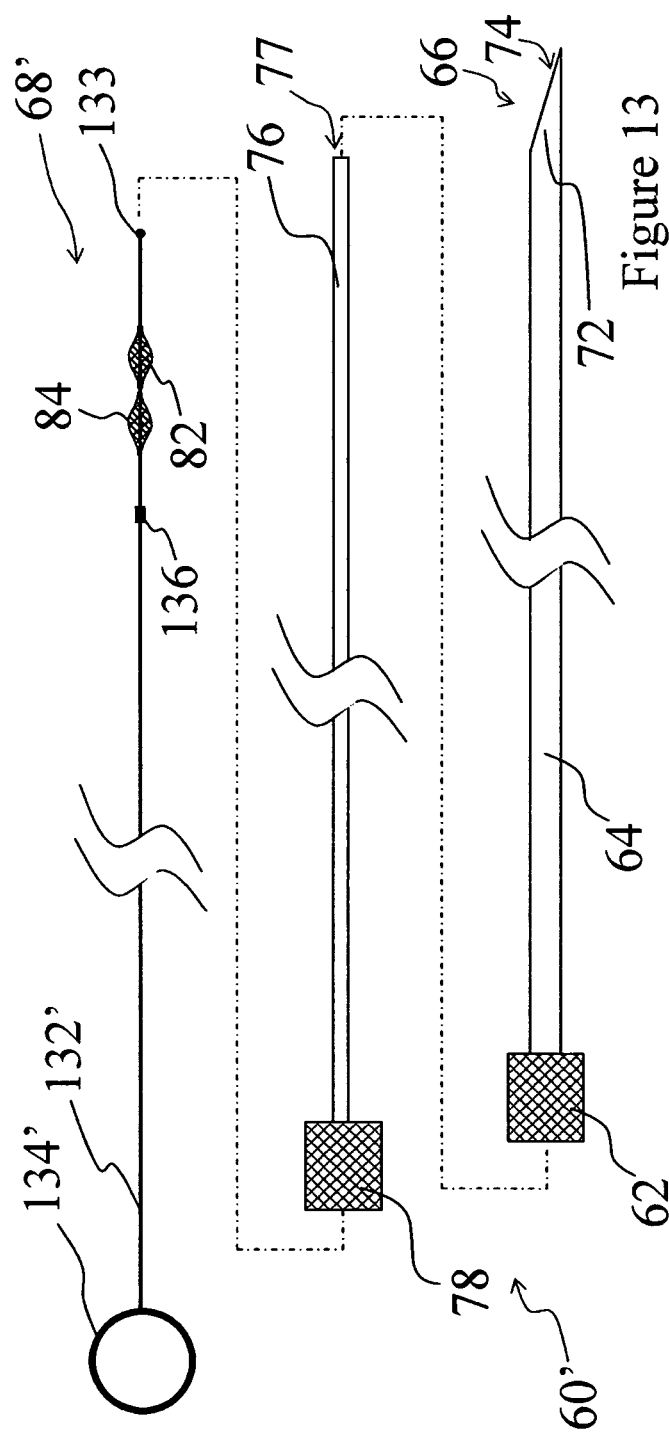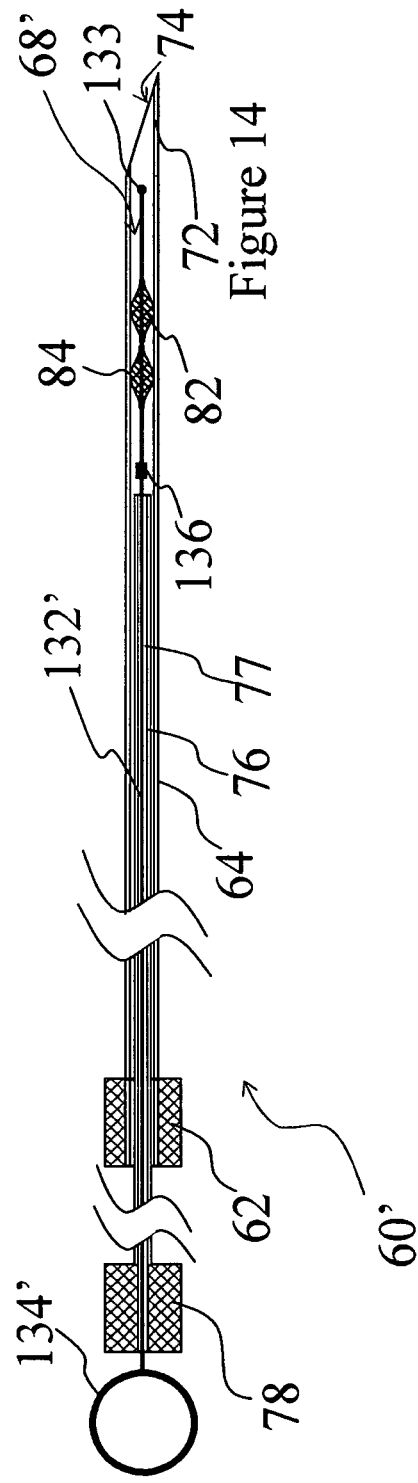

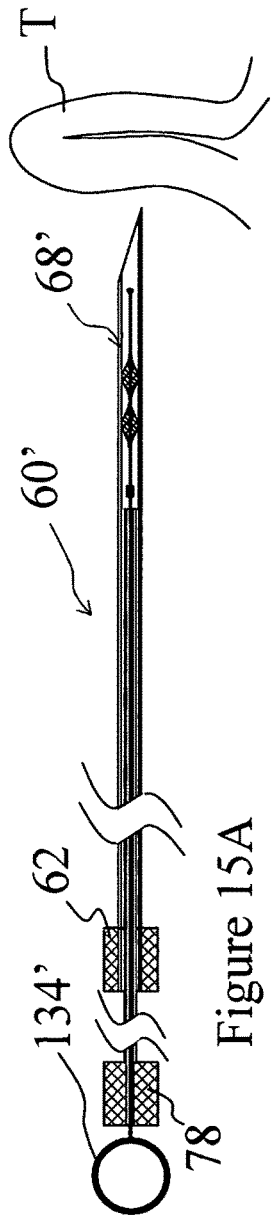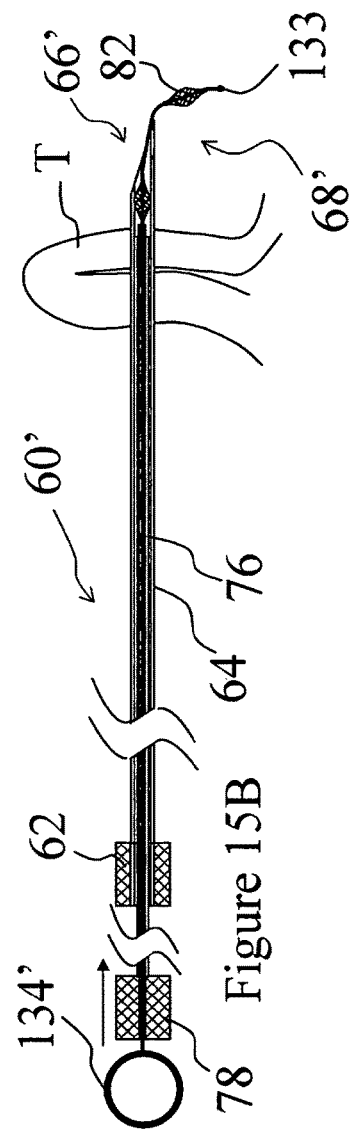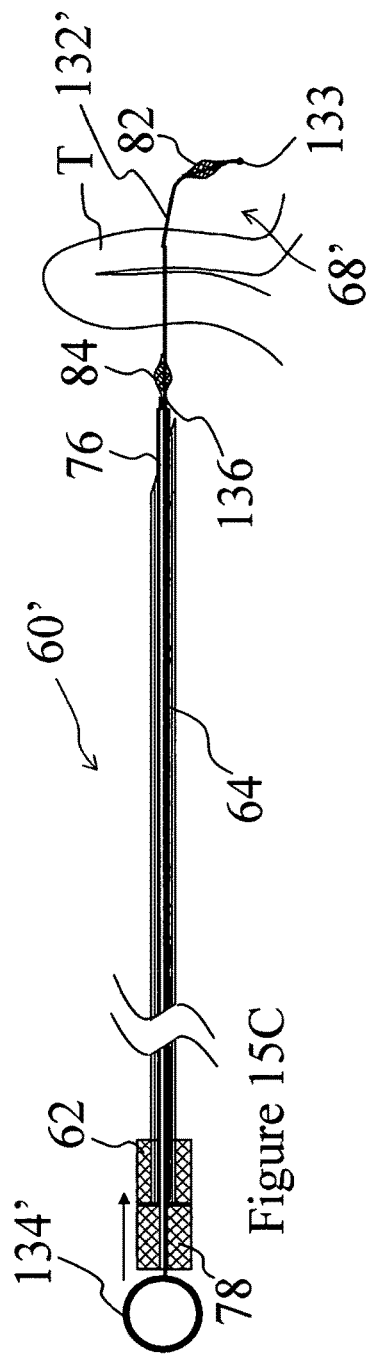

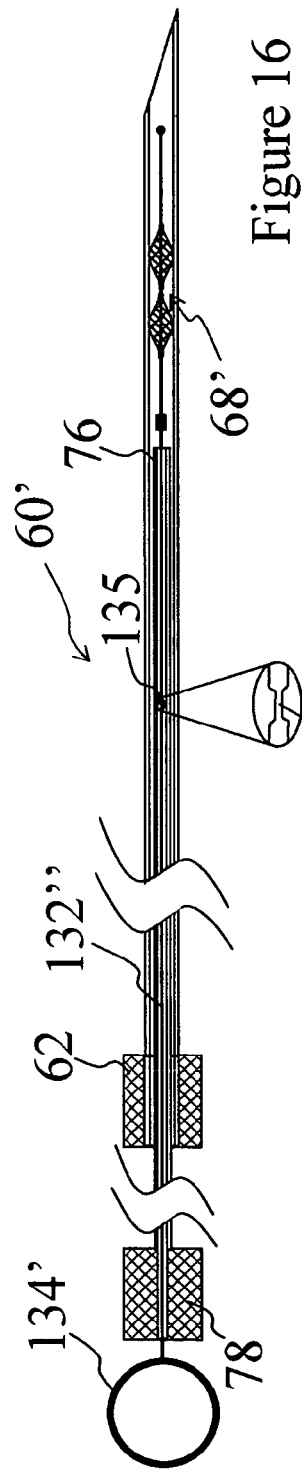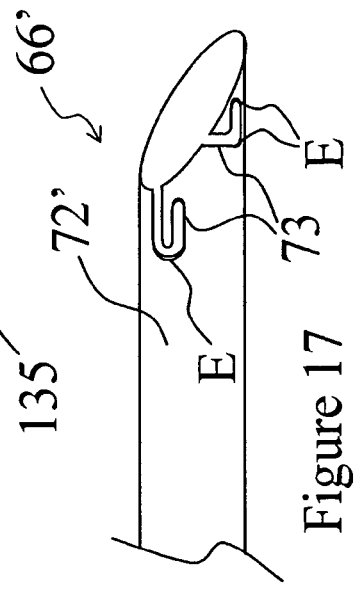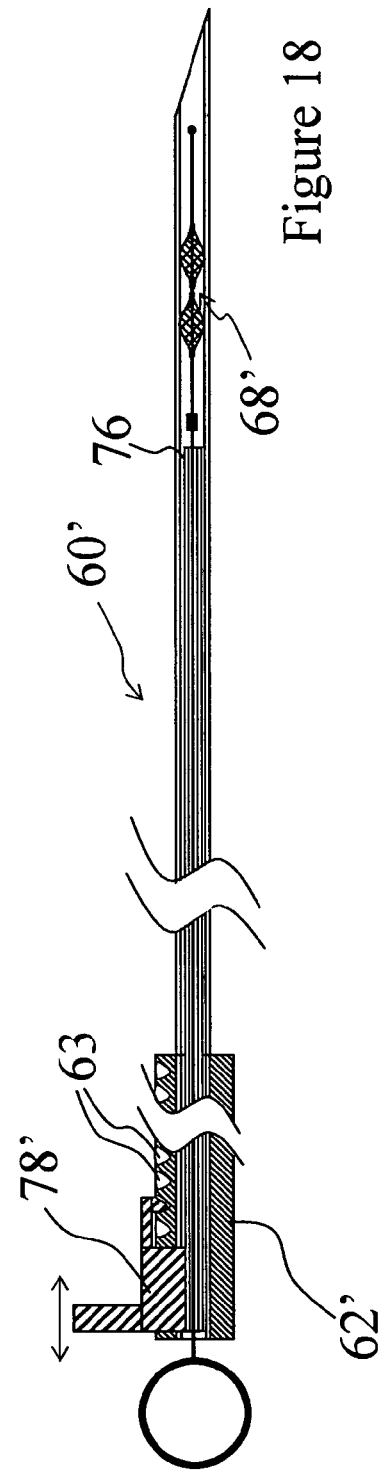

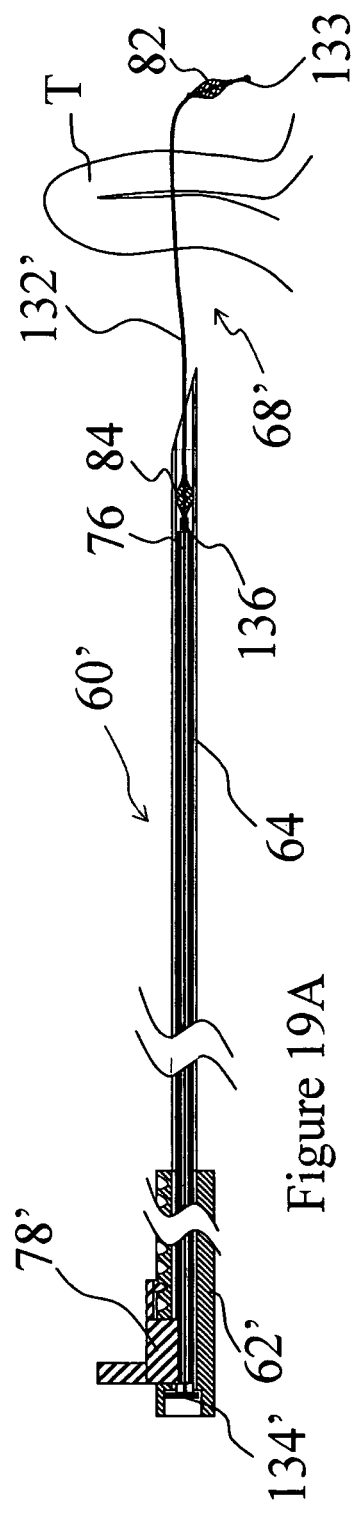
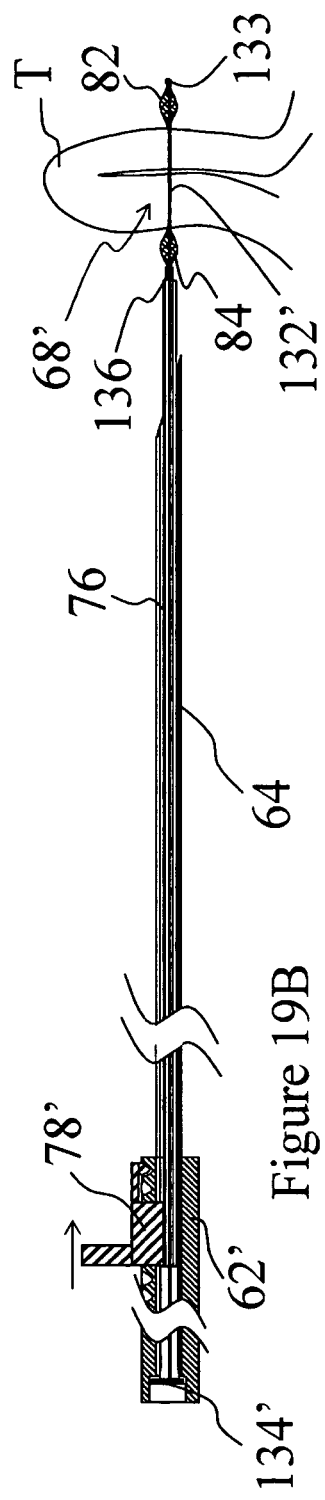
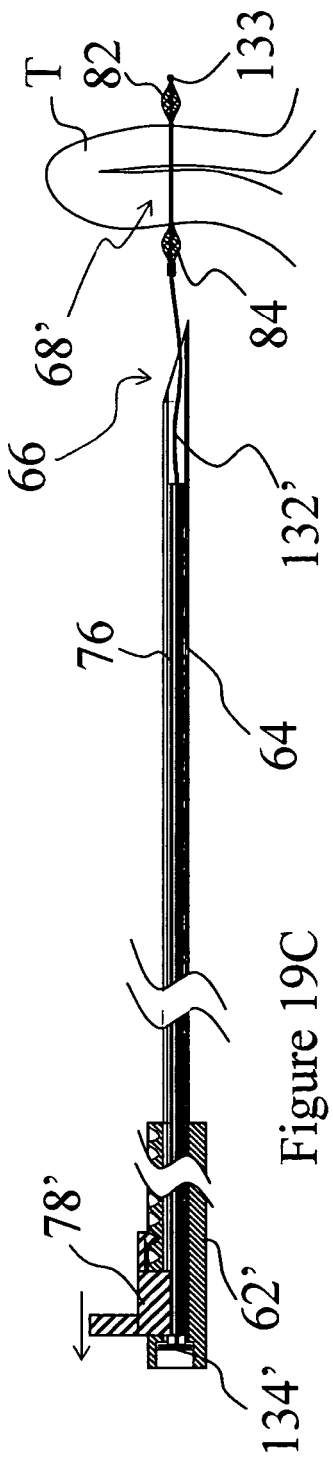
Figure 19A
Figure 19B
Figure 19C

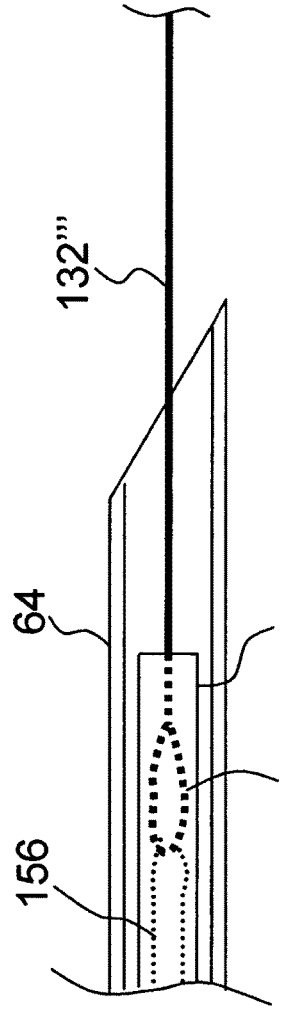
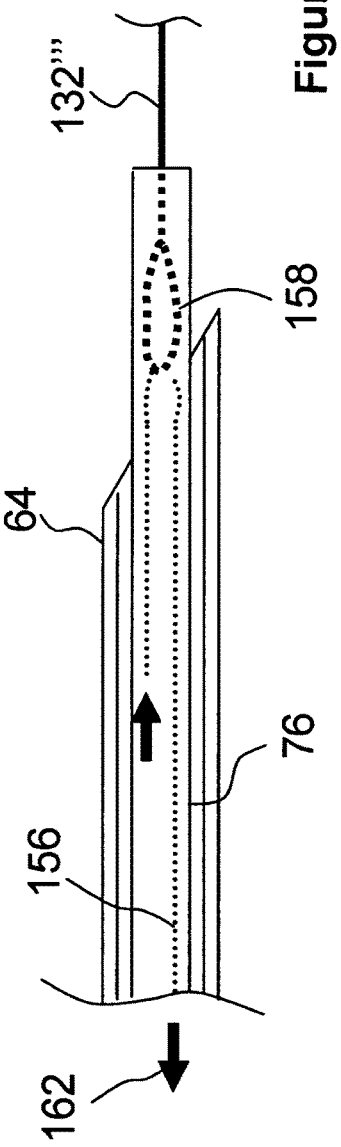
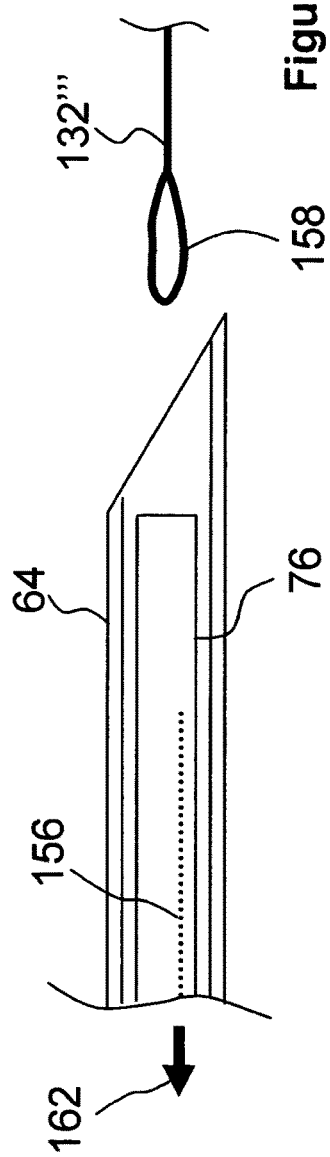

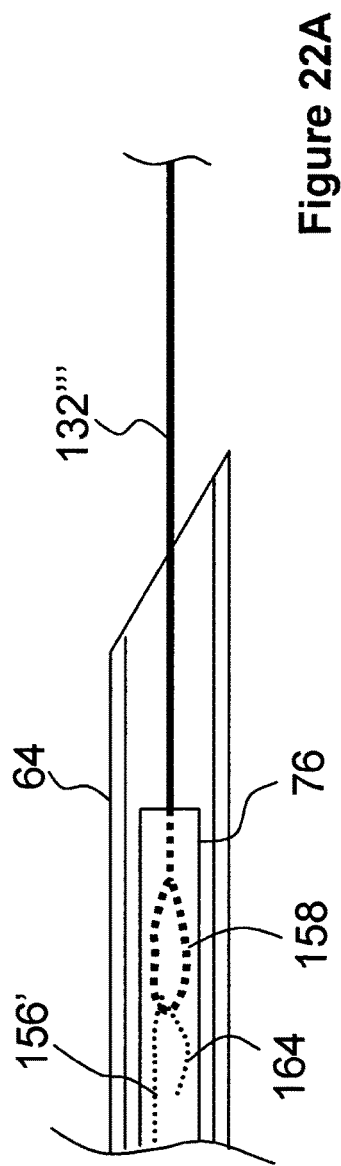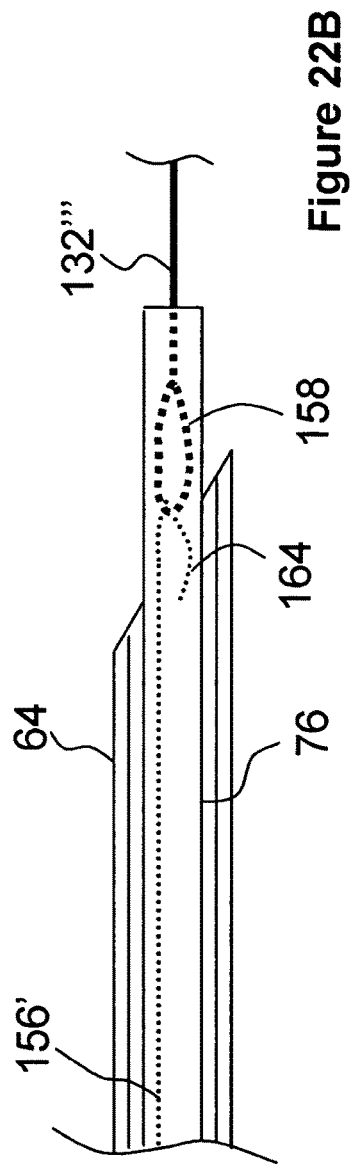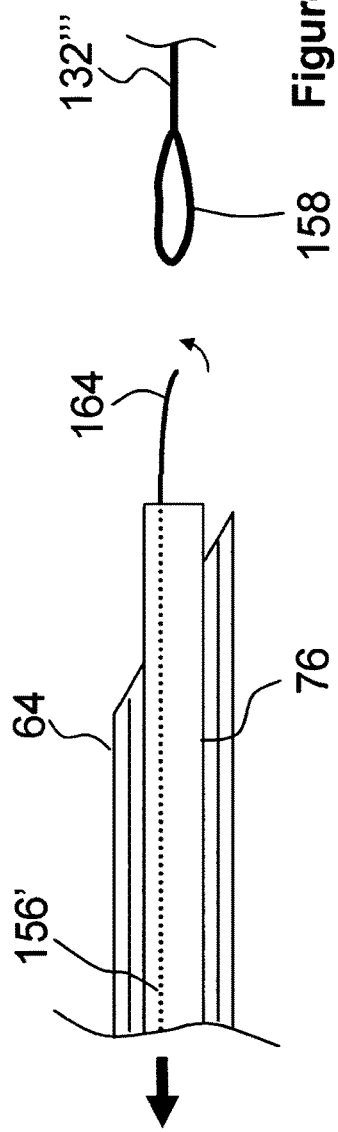

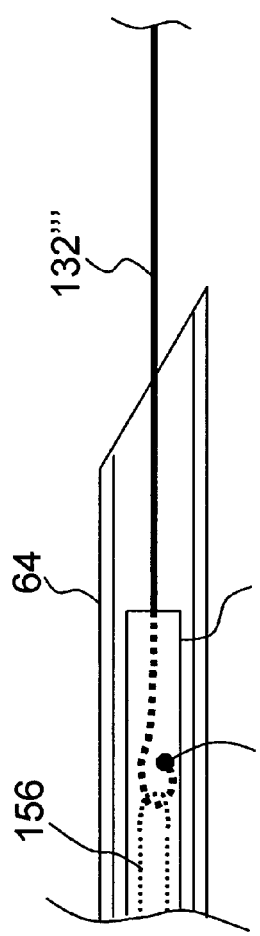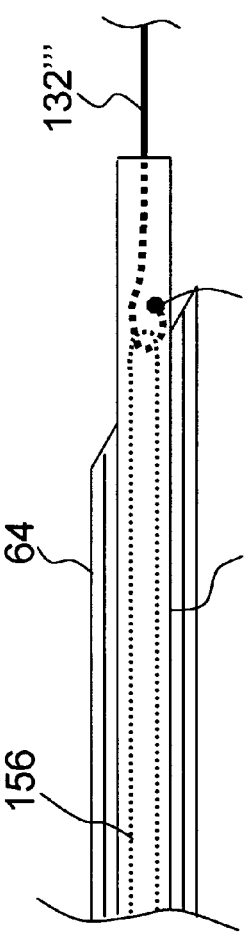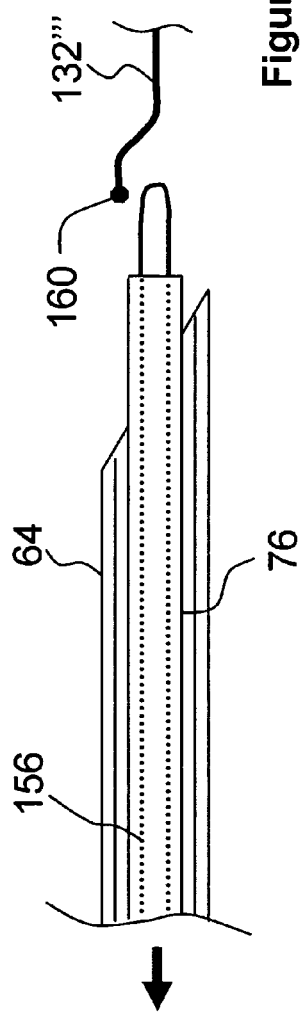

METHODS AND APPARATUS FOR SECURING AND DEPLOYING TISSUE ANCHORS

BACKGROUND OF THE INVENTION

Field of the Invention

The present invention relates to methods and apparatus for securing and deploying tissue anchors. More particularly, the present invention relates to methods and apparatus for endoluminally or laparoscopically securing and deploying anchors within or against tissue, for instance, to form and/or secure tissue folds or to approximate regions of tissue, etc.

A number of surgical techniques have been developed to treat various gastrointestinal disorders. One such example of a pervasive disorder is morbid obesity. Conventional surgical treatment for morbid obesity typically includes, e.g., bypassing an absorptive surface of the small intestine, or reducing the stomach size. However, many conventional surgical procedures may present numerous life-threatening post-operative complications, and may cause atypical diarrhea, electrolytic imbalance, unpredictable weight loss and reflux of nutritious chyme proximal to the site of the anastomosis.

Furthermore, the sutures or staples that are often used in surgical procedures for gastrointestinal disorders typically require extensive training by the clinician to achieve competent use, and may concentrate significant force over a small surface area of the tissue, thereby potentially causing the suture or staple to tear through the tissue. Many of the surgical procedures require regions of tissue within the body to be approximated towards one another and reliably secured. The gastrointestinal lumen, for instance, includes four tissue layers, where the mucosa layer is the inner-most tissue layer followed by connective tissue, the muscularis layer, and where the serosa layer is the outer-most tissue layer.

One problem with conventional gastrointestinal reduction systems is that the anchors (or staples) should engage at least the muscularis tissue layer in order to provide a proper foundation. In other words, the mucosa and connective tissue layers typically are not strong enough to sustain the tensile loads imposed by normal movement of the stomach wall during ingestion and processing of food. In particular, these layers tend to stretch elastically rather than firmly hold the anchors (or staples) in position, and accordingly, the more rigid muscularis and/or serosa layer should ideally be engaged. This problem of capturing the muscularis or serosa layers becomes particularly acute where it is desired to place an anchor or other apparatus transesophageally rather than intra-operatively, since care must be taken in piercing the tough stomach wall not to inadvertently puncture adjacent tissue or organs.

One conventional method for securing anchors within a body lumen to the tissue is to utilize sewing devices to suture the stomach wall into folds. This procedure typically involves advancing a sewing instrument through the working channel of an endoscope and into the stomach and against the stomach wall tissue. The contacted tissue is then typically drawn into the sewing instrument where one or more sutures or tags are implanted to hold the suctioned tissue in a folded condition known as a plication. Another method involves manually creating sutures for securing the plication.

One of the problems associated with these types of procedures is the time and number of intubations needed to perform the various procedures endoscopically. Another problem is the time required to complete a plication from the surrounding tissue with the body lumen. In the period of time that a patient is anesthetized, procedures such as for the treatment of morbid obesity or for GERD must be performed to completion. Accordingly, the placement and securement of the tissue plication should ideally be relatively quick and performed with a minimal level of confidence.

Another problem with conventional methods involves ensuring that the staple, knotted suture, or clip is secured tightly against the tissue and that the newly created plication will not relax under any slack which may be created by slipping staples, knots, or clips. Other conventional tissue securement devices such as suture anchors, twist ties, crimps, etc. are also often used to prevent sutures from slipping through tissue. However, many of these types of devices are typically large and unsuitable for low-profile delivery through the body, e.g., transesophageally.

Moreover, when grasping or clamping onto or upon the layers of tissue with conventional anchors, sutures, staples, clips, etc., many of these devices are configured to be placed only after the tissue has been plicated and not during the actual plication procedure.

BRIEF SUMMARY OF THE INVENTION

An example of a tool which may be utilized for endoluminally accessing tissue may generally comprise a flexible catheter or tubular body which may be configured to be sufficiently flexible for advancement into a body lumen, e.g., transorally, percutaneously, laparoscopically, etc. The tubular body may be configured to be torqueable such that when a control handle is manipulated and/or rotated by a practitioner from outside the patient's body, the longitudinal and/or torquing force is transmitted along the flexible body such that the distal end of body is advanced, withdrawn, or rotated in a corresponding manner.

A tissue manipulation assembly may be located at the distal end of the tubular body and is generally used to contact and form tissue folds, as mentioned above. The tissue manipulation assembly may be connected to the distal end of the tubular body via a pivotable coupling, and a lower jaw member may extend distally from the pivotable coupling with an upper jaw member, in this example, pivotably coupled to the lower jaw member via a jaw pivot. The location of the jaw pivot may be positioned at various locations along the lower jaw depending upon a number of factors, e.g., the desired size of the "bite" or opening for accepting tissue between the jaw members, the amount of closing force between the jaw members, etc. One or both jaw members may also have a number of protrusions, projections, grasping teeth, textured surfaces, etc., on the surface or surfaces of the jaw members to facilitate the adherence of tissue therebetween.

A launch tube may extend from the handle, through tubular body, and distally from the end of tubular body where a distal end of the launch tube is pivotally connected to the upper jaw member at a pivot. A distal portion of the launch tube may be pivoted into position within a channel or groove defined in upper jaw member to facilitate a low-profile configuration of the tissue manipulation assembly. When articulated, either via the launch tube or other mechanism, the jaw members may be urged into an open configuration to receive tissue in the jaw opening between the jaw members.

In operation, a shape-lockable endoscopic assembly may be advanced into a patient's stomach per-orally and through the esophagus. Such an endoscopic assembly may generally comprise an endoscopic device, which may have a distal portion that may be articulated and steered to position its distal end anywhere within the stomach. Once desirably configured, the assembly may then be locked or rigidized to maintain its shape or configuration to allow for procedures to be performed on the tissue utilizing any number of tools delivered therethrough.

The tissue manipulation assembly may be delivered into the patient while in a low-profile configuration, e.g., transorally, through the shape-lockable endoscopic assembly, through an endoscope, an endoscopic device, or directly. Once desirably positioned, the launch tube may be urged proximally via its proximal end at handle. Because the jaw assembly pivot and the relative positioning of the upper jaw pivot along lower jaw member and launch tube pivot along upper jaw member, the proximal movement of the launch tube may effectively articulate upper jaw into an expanded jaw configuration. Proximally urging the launch tube may also urge the lower jaw member to pivot about the assembly pivot and form an angle relative to a longitudinal axis of the tubular body. The opening of the upper jaw relative to the lower jaw creates a jaw opening for grasping or receiving tissue. Moreover, the tissue manipulation assembly may also include a stop located adjacent to the jaw assembly pivot or within the pivot itself.

A second tool for initially engaging the tissue region of interest may also be deployed and utilized to engage the tissue and to position the engaged tissue between the jaws of the jaw assembly. Any number of tools may be used in combination with the tissue manipulation assembly. Once the tissue has been engaged between the jaw members, a needle assembly may be urged through the launch tube to pierce through the grasped tissue. Once the needle assembly has been passed through the engaged tissue, one or more tissue anchors may be deployed for securing the tissue.

BRIEF DESCRIPTION OF THE DRAWINGS

FIGS. 8A to 8D illustrate an example for performing an endoluminal tissue manipulation and securement procedure utilizing a tissue manipulation assembly in combination with a separate tissue grasping tool within, e.g., a patient's stomach.

FIG. 9A shows one variation where a single tissue fold may be secured between tissue anchors using the tissue manipulation assembly.

FIG. 9B shows another variation where two or more tissue folds may be secured between tissue anchors using the tissue manipulation assembly.

FIG. 13 illustrates an exploded view of a variation of an anchor assembly and needle deployment assembly.

FIG. 14 illustrates an assembly view, partially in section, of the anchor assembly and needle deployment assembly variation of FIG. 13.

FIGS. 15A to 15F illustrate an exemplary method of using the anchor assembly and needle deployment assembly variation of FIGS. 13 and 14.

FIG. 16 illustrates a variation of the suture element for use with the anchor assembly and needle deployment assembly of FIGS. 13 to 15.

FIG. 17 illustrates a variation of the needle for use with the anchor assembly and needle deployment assembly variation of FIGS. 13 to 15.

FIG. 18 illustrates a variation of the control mechanisms for use with the needle deployment assemblies of FIGS. 13 to 17.

FIGS. 19A to 19C illustrate an exemplary method of using another variation of the anchor assembly and needle deployment assembly.

FIGS. 21A to 21C illustrate another variation of the needle deployment assembly utilizing a release suture or wire which may be routed through a looped terminal end of a suture element.

FIGS. 22A to 22C illustrate yet another variation of the needle deployment assembly utilizing a reconfigurable hook element which may configure itself from a hooked configuration to an open or straightened configuration.

FIGS. 23A to 23C illustrate yet another variation of the needle deployment assembly utilizing a release suture or wire with an obstructive element to be released from the release suture or wire.

DETAILED DESCRIPTION OF THE INVENTION

In manipulating tissue or creating tissue folds, a having a distal end effector may be advanced endoluminally, e.g., transorally, transgastrically, etc., into the patient's body, e.g., the stomach. The tissue may be engaged or grasped and the engaged tissue may be manipulated by a surgeon or practitioner from outside the patient's body. Examples of creating and forming tissue plications may be seen in further detail in U.S. patent application Ser. No. 10/955,245 filed Sep. 29, 2004, which has been incorporated herein by reference above, as well as U.S. patent application Ser. No. 10/735,030 filed Dec. 12, 2003, which is incorporated herein by reference in its entirety.

In engaging, manipulating, and/or securing the tissue, various methods and devices may be implemented. For instance, tissue securement devices may be delivered and positioned via an endoscopic apparatus for contacting a tissue wall of the gastrointestinal lumen, creating one or more tissue folds, and deploying one or more tissue anchors through the tissue fold(s). The tissue anchor(s) may be disposed through the muscularis and/or serosa layers of the gastrointestinal lumen.

Figure 1A:
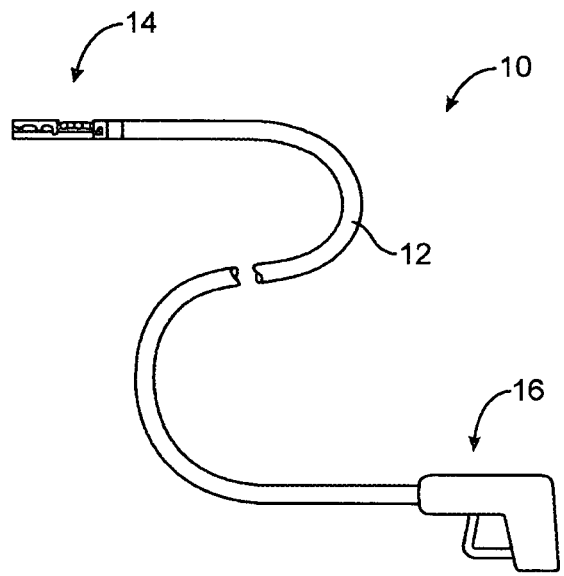
FIG. 1A shows a side view of one variation of a tissue manipulation assembly having a flexible body and a handle.

An illustrative side view of one example of a tool which may be utilized for endoluminally accessing tissue is shown in FIG. 1A, which shows assembly 10. The assembly 10 generally comprises a flexible catheter or tubular body 12 which may be configured to be sufficiently flexible for advancement into a body lumen, e.g., transorally, percutaneously, laparoscopically, etc. Tubular body 12 may be configured to be torqueable through various methods, e.g., utilizing a braided tubular construction, such that when handle 16 is manipulated and/or rotated by a practitioner from outside the patient's body, the longitudinal and/or torquing force is transmitted along body 12 such that the distal end of body 12 is advanced, withdrawn, or rotated in a corresponding manner.

Figure 1B:
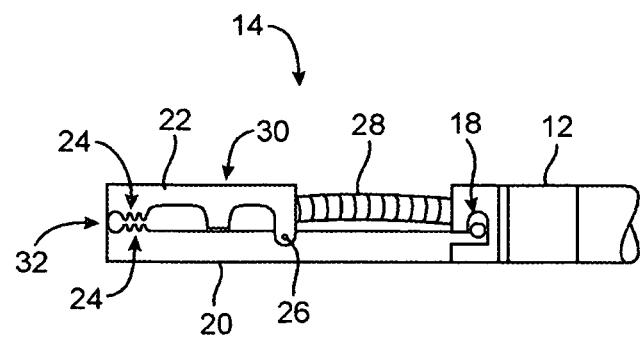
FIG. 1B illustrates a detail side view of a tissue manipulation assembly in a low-profile configuration connected to the distal end of the tubular body via a pivotable coupling.

Tissue manipulation assembly 14 is located at the distal end of tubular body 12 and is generally used to contact and form tissue folds, as mentioned above. FIG. 1B shows an illustrative detail side view in which tissue manipulation assembly 14 may be seen connected to the distal end of tubular body 12 via a pivotable coupling 18. Lower jaw member 20 extends distally from the pivotable coupling 18 and upper jaw member 22, in this example, may be pivotably coupled to lower jaw member 20 via jaw pivot 26. The location of jaw pivot 26 may be positioned at various locations along lower jaw 20 depending upon a number of factors, e.g., the desired size of the "bite" or opening for accepting tissue between the jaw members, the amount of closing force between the jaw members, etc. One or both jaw members 20, 22 may also have a number of protrusions, projections, grasping teeth, textured surfaces, etc., 24 on the surface or surfaces of the jaw members 20, 22 facing one another to facilitate the adherence of tissue between the jaw members 20, 22.

Launch tube 28 may extend from handle 16, through tubular body 12, and distally from the end of tubular body 12 where a distal end of launch tube 28 is pivotally connected to upper jaw member 22 at launch tube pivot 30. A distal portion of launch tube 28 may be pivoted into position within a channel or groove defined in upper jaw member 22, to facilitate a low-profile configuration of tissue manipulation assembly 14. When articulated, either via launch tube 28 or other mechanism, as described further below, jaw members 20, 22 may be urged into an open configuration to receive tissue in jaw opening 32 between the jaw members 20, 22.

Launch tube 28 may be advanced from its proximal end at handle 16 such that the portion of launch tube 28, which extends distally from body 12, is forced to rotate at hinge or pivot 30 and reconfigure itself such that the exposed portion forms a curved or arcuate shape that positions the launch tube opening perpendicularly relative to upper jaw member 22. Launch tube 28, or at least the exposed portion of launch tube 28, may be fabricated from a highly flexible material or it may be fabricated, e.g., from Nitinol tubing material which is adapted to flex, e.g., via circumferential slots, to permit bending.

Figure 2A:
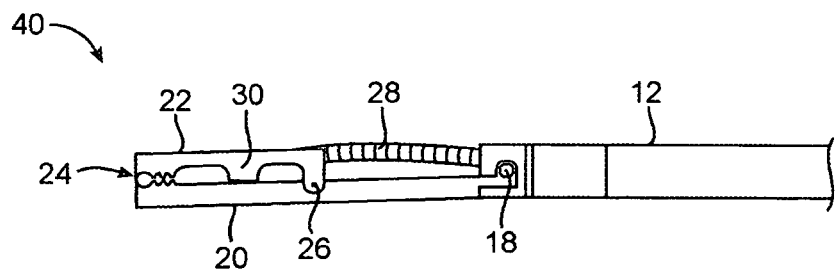
FIGS. 2A to 2C illustrate a method for articulating the tissue manipulation assembly from a low-profile configuration to an opened configuration and to a closed jaw configuration for clamping upon tissue, respectively.
Figure 2B:
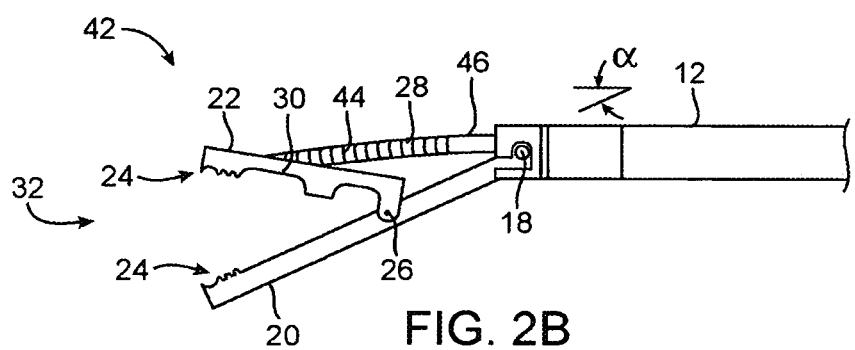
Figure 2C:
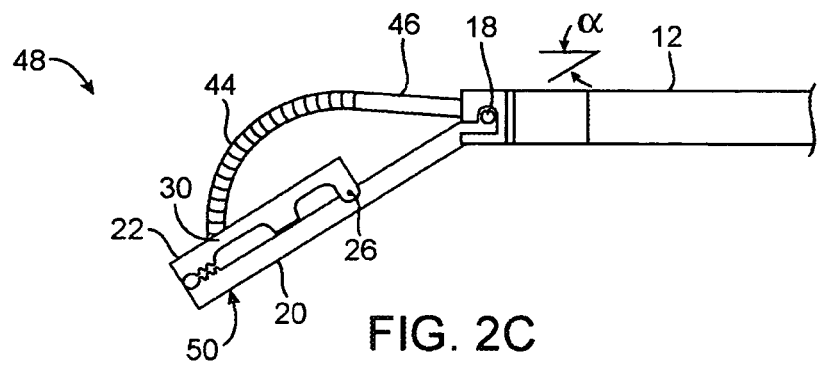

FIGS. 2A to 2C illustrate one method for articulating a tissue manipulation assembly into an opened and closed configuration. As shown in FIG. 2A, the assembly may be delivered into a patient while in a low-profile configuration 40, e.g., transorally, through an endoscope, an endoscopic device, or directly. Once desirably positioned, launch tube 28 may be urged proximally via its proximal end at handle 16. Because of jaw assembly pivot 18 and the relative positioning of upper jaw pivot 26 along lower jaw member 20 and launch tube pivot 30 along upper jaw member 22, the proximal movement of launch tube 28 may effectively articulate upper jaw 22 into an expanded jaw configuration 42, as shown in FIG. 2B. Proximally urging launch tube 28 may also urge lower jaw member 20 to pivot about assembly pivot 18 and form an angle, a, relative to a longitudinal axis of tubular body 12. The opening of upper jaw 22 relative to lower jaw 20 creates jaw opening 32 for grasping or receiving tissue. Moreover, the tissue manipulation assembly may also include a stop located adjacent to jaw assembly pivot 18 or within the pivot 18 itself.

Once launch tube 28 has been urged proximally, it may be locked into place thus locking the jaw configuration as well. Moreover, having the launch tube 28 articulate the jaw members 20, 22 in this variation eliminates the need for a separate jaw articulation and/or locking mechanism. Once the tissue has been pulled or manipulated between jaw members 20, 22, launch tube 28 may be pushed distally to actuate the jaw members 20, 22 into a closed, grasping configuration 48, as shown in FIG. 2C, for engagement with the tissue. As launch tube 28 is urged distally through body 12, lower jaw member 20 may be maintained at the angle, α, relative to the tissue to further facilitate manipulation of the grasped tissue.

Launch tube 28 may further define a flexible portion 44 distally of a rigid portion 46. Although launch tube 28 may be fabricated from different materials having differing flexibilities, it may also be fabricated from a single material, as mentioned above, where the flexible portion 44 may be configured, e.g., by slotting, to allow for bending of the launch tube 28 in a plane to form a single curved or arcuate section while the rigid section 46 may extend at least partially into tubular body 12 to provide column strength to launch tube 28 while it is urged distally upon upper jaw member 22 and upon any tissue engaged thereby, as seen in the FIG. 2C.

Once the tissue has been engaged between jaw members 20, 22, a needle assembly may be urged through handle 16 and out through launch tube 28. The needle assembly may pass through lower jaw member 20 via needle assembly opening 50 defined in lower jaw member 20 to pierce through the grasped tissue. Once the needle assembly has been passed through the engaged tissue, one or more tissue anchors may be deployed for securing the tissue, as described in further detail in U.S. patent application Ser. No. 10/955,245, which has been incorporated by reference above.

Figure 3A:
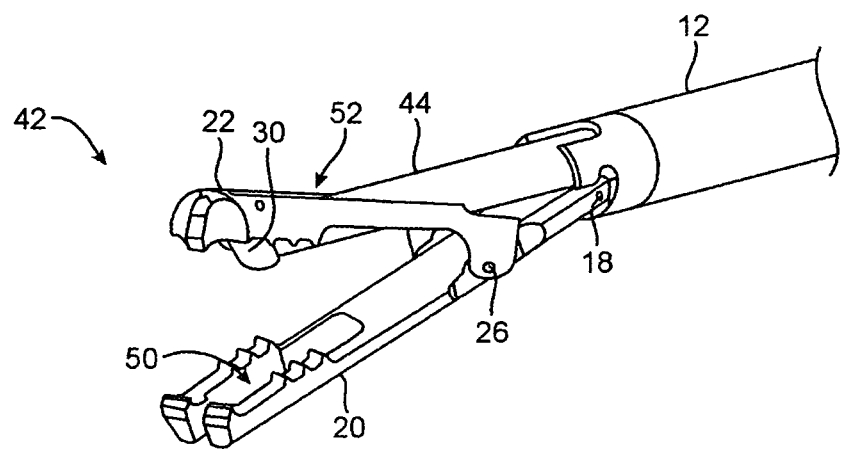
FIGS. 3A and 3B show detail perspective views of the tissue manipulation assembly in an open and clamped configuration, respectively.
Figure 3B:
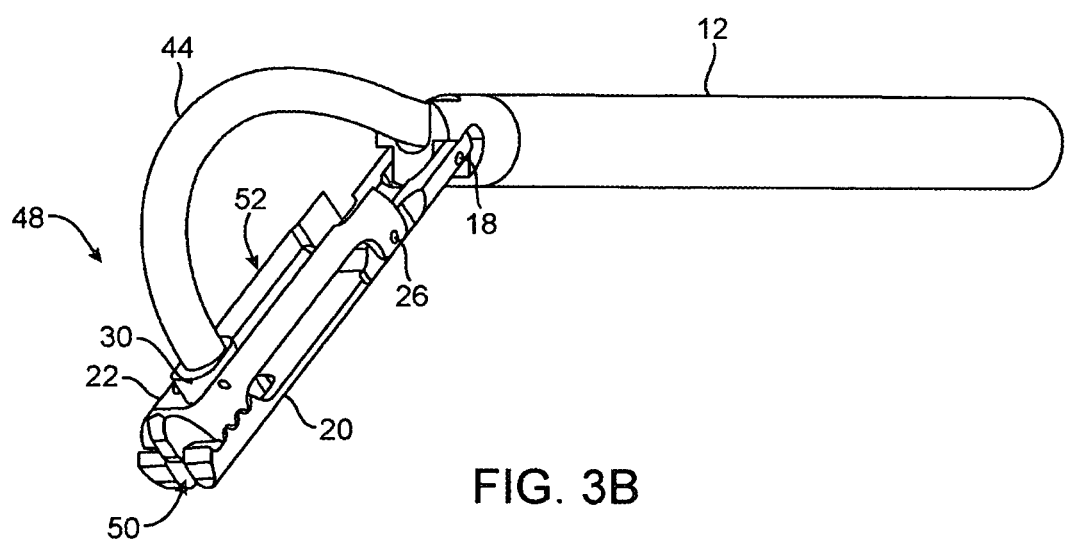

FIGS. 3A and 3B show detail perspective views of the tissue manipulation assembly. As shown in FIG. 3A, lower jaw member 20 and upper jaw member 22 may be seen its open configuration 42 when the launch tube has been urged proximally. Launch tube channel 52 may also be seen defined within upper jaw member 22 for providing a space for positioning the launch tube when in the low-profile configuration. Also shown is needle assembly opening 50 defined within lower jaw member 20 for passage of the needle assembly therethrough. FIG. 3B shows the assembly in its closed jaw configuration where the launch tube has been urged distally in which it rotates about launch tube pivot 30 such that the opening the launch tube become perpendicular relative to the jaw members 20, 22.

Although one particular variation of the jaw members 20, 22 is shown, this is not intended to be limiting in jaw member configuration or operation. Other variations may include various placement of the jaws relative to one another, alternative configurations for articulating the jaw members, alternative configurations for the launch tube placement, etc. Other variations are intended to be within the scope of this disclosure.

Figure 4:
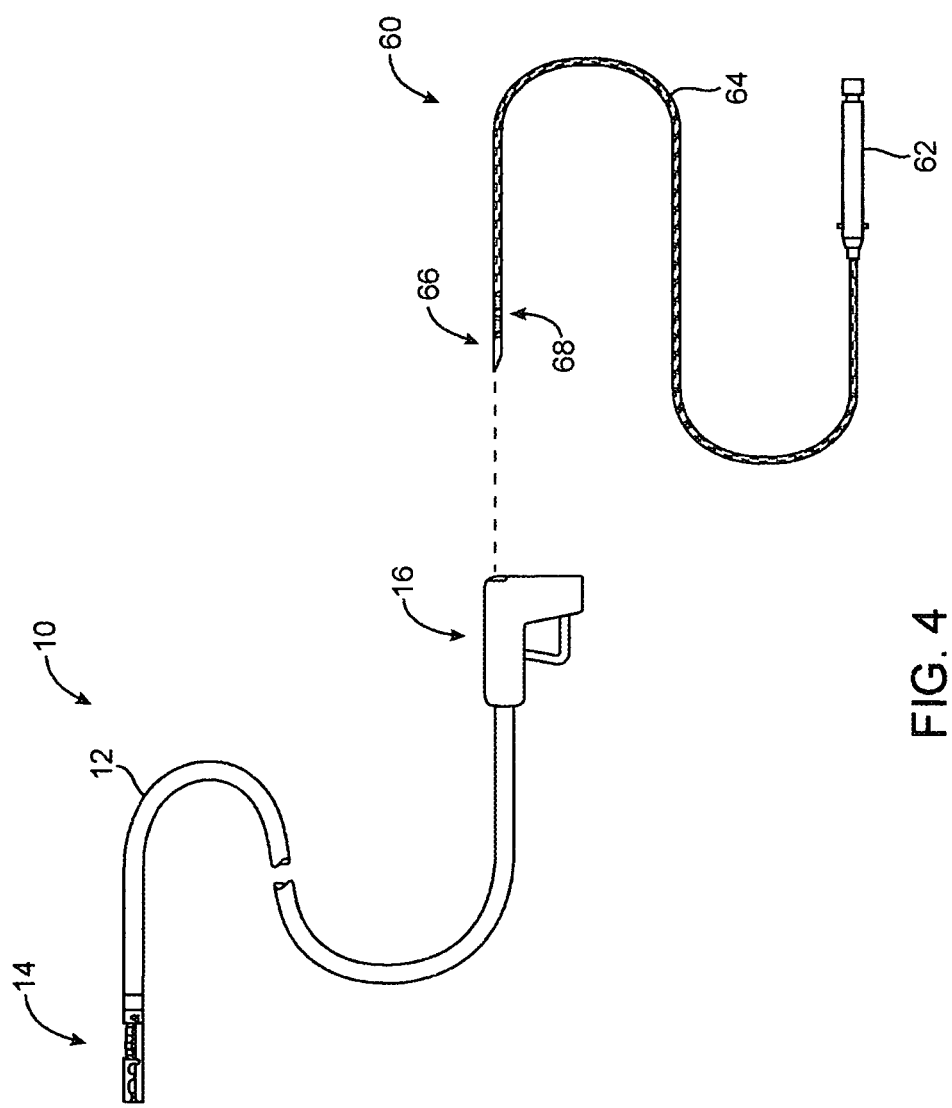
FIG. 4 shows an assembly view of how a needle deployment assembly may be introduced through a handle and tubular body of the tissue manipulation assembly.

As mentioned above, a needle deployment assembly 60 may be deployed through the assembly 10 by introducing needle deployment assembly 60 into the handle 16 and through tubular body 12, as shown in the assembly view of FIG. 4, such that the needle assembly 66 is advanced from the launch tube and into or through approximated tissue. Once the needle assembly 66 has been advanced through the tissue, the anchor assembly 68 may be deployed or ejected. Anchor assembly 68 is normally positioned within the distal portion of tubular sheath 64, which extends from needle assembly control or housing 62. Once the anchor assembly 68 has been fully deployed from sheath 64, the spent needle deployment assembly 60 may be removed from assembly 10 and another needle deployment assembly may be introduced without having to remove assembly 10 from the patient. The length of sheath 64 is such that it may be passed entirely through the length of tubular body 12 to enable the deployment of needle assembly 66 into and/or through the tissue.

Figure 5A:
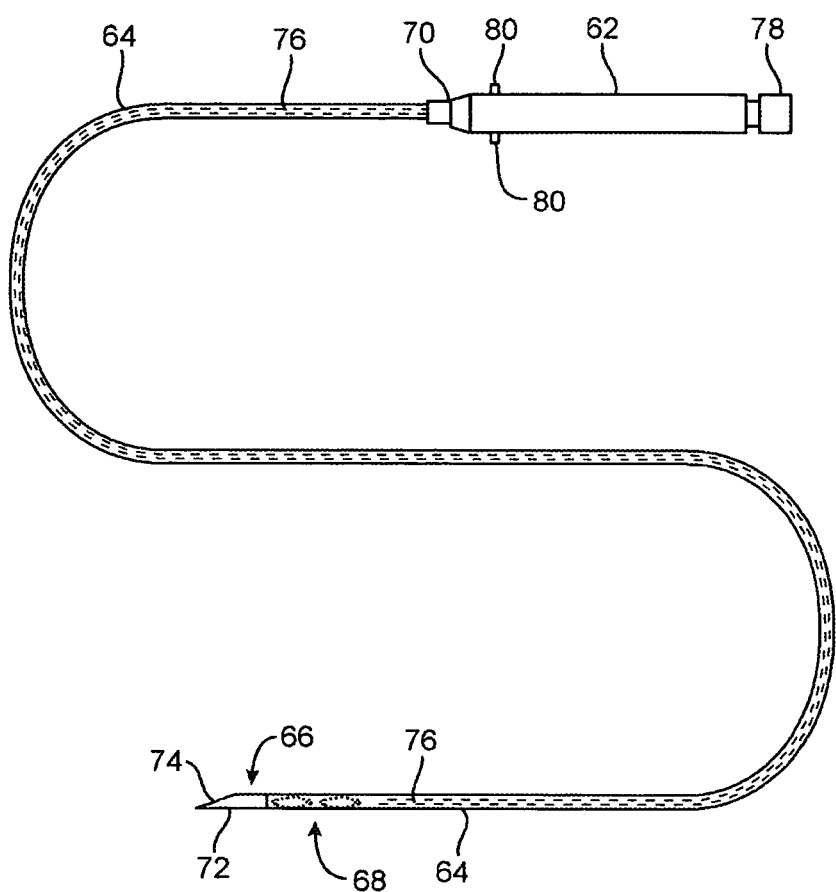
FIG. 5A shows a detailed assembly view of the needle deployment assembly from FIG. 4.

FIG. 5A shows a detailed assembly view of the needle deployment assembly 60 from FIG. 4. In this variation, elongate and flexible sheath or catheter 64 may extend removably from needle assembly control or housing 62. Sheath or catheter 64 and housing 62 may be interconnected via interlock 70 which may be adapted to allow for the securement as well as the rapid release of sheath 64 from housing 62 through any number of fastening methods, e.g., threaded connection, press-fit, releasable pin, etc. Needle body 72, which may be configured into any one of the variations described above, may extend from the distal end of sheath 64 while maintaining communication between the lumen of sheath 64 and needle opening 74.

Figure 5B:
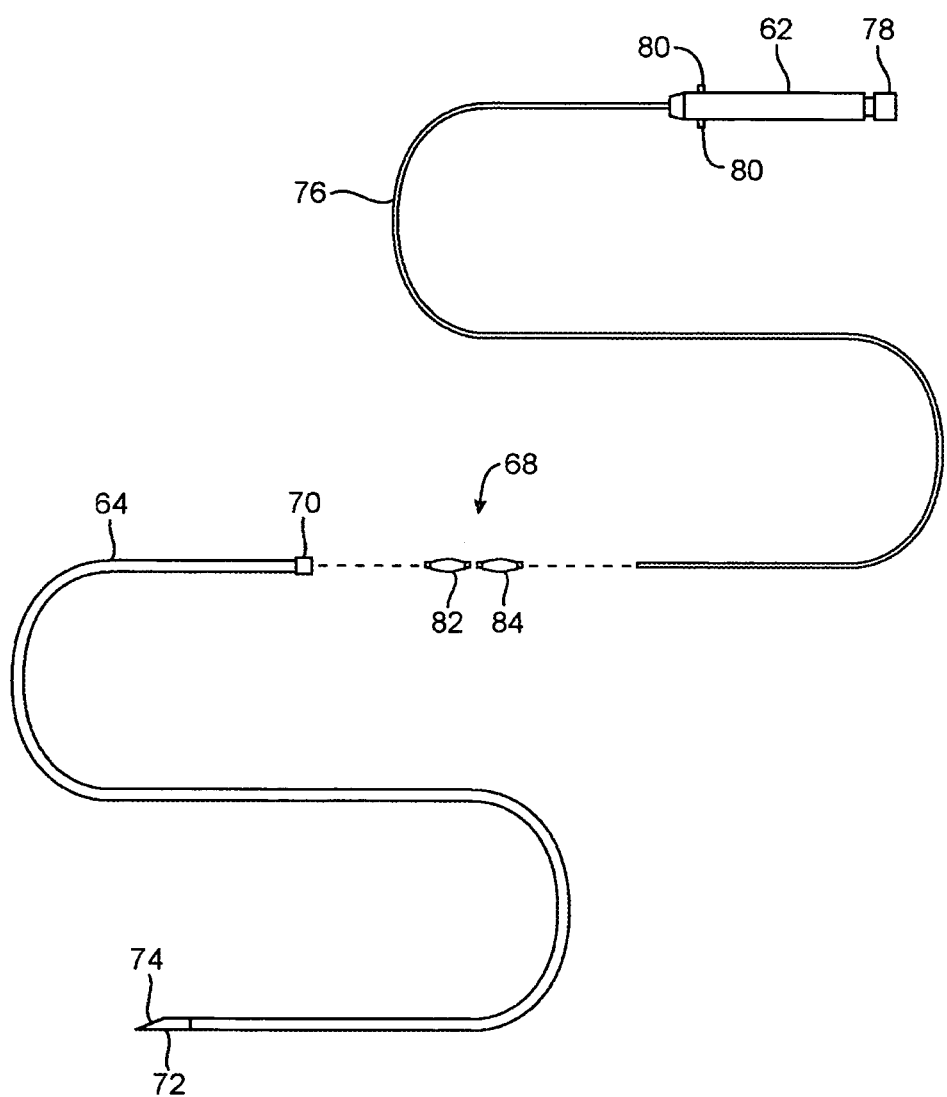
FIG. 5B shows an exploded assembly view of the needle deployment assembly from FIG. 5A.

Elongate pusher 76 may comprise a flexible wire or hypotube which is translationally disposed within sheath 64 and movably connected within housing 62. A proximally-located actuation member 78 may be rotatably or otherwise connected to housing 62 to selectively actuate the translational movement of elongate pusher 76 relative to sheath 64 for deploying the anchors from needle opening 74. Anchor assembly 68 may be seen positioned distally of elongate pusher 76 within sheath 64 for deployment from sheath 64. Needle assembly guides 80 may also be seen protruding from housing 62 for guidance through the locking mechanism described above. FIG. 5B shows an exploded assembly view of the needle deployment assembly 60 from FIG. 5A. As seen, sheath 64 may be disconnected from housing 62 via interlock 70 to reveal the elongate pusher 76 connected to housing 62 and the distal and proximal anchors 82, 84, respectively, of anchor assembly 68.

With respect to the anchor assemblies, the types of anchors shown and described are intended to be illustrative and are not limited to the variations shown. For instance, the tissue anchor variations may also include "T"-type anchors while other variations may include reconfigurable "basket"-type anchors, which may generally comprise a number of configurable struts or legs extending between at least two collars or support members or reconfigurable mesh structures extending between the two collars. Other variations of these or other types of anchors are also contemplated for use in an anchor assembly. Moreover, a single type of anchor may be used exclusively in an anchor assembly; alternatively, a combination of different anchor types may be used in an anchor assembly. Furthermore, the different types of cinching or locking mechanisms are not intended to be limited to any of the particular variations shown and described but may be utilized in any of the combinations or varying types of anchors as practicable.

Other variations for the needle assemblies and for the anchors are described in further detail in U.S. patent application Ser. No. 10/955,245, which has been incorporated by reference above.

In operation when manipulating and securing tissue within a patient's body, a separate elongate shaft having a tool on or near the distal end of the shaft may be utilized in conjunction with the tissue manipulation assembly 14. Such tools are generally utilized in endoluminal procedures where the tools are delivered through an endoscope. Generally, several different tools may be utilized for performing a procedure endoluminally.

Figure 6:
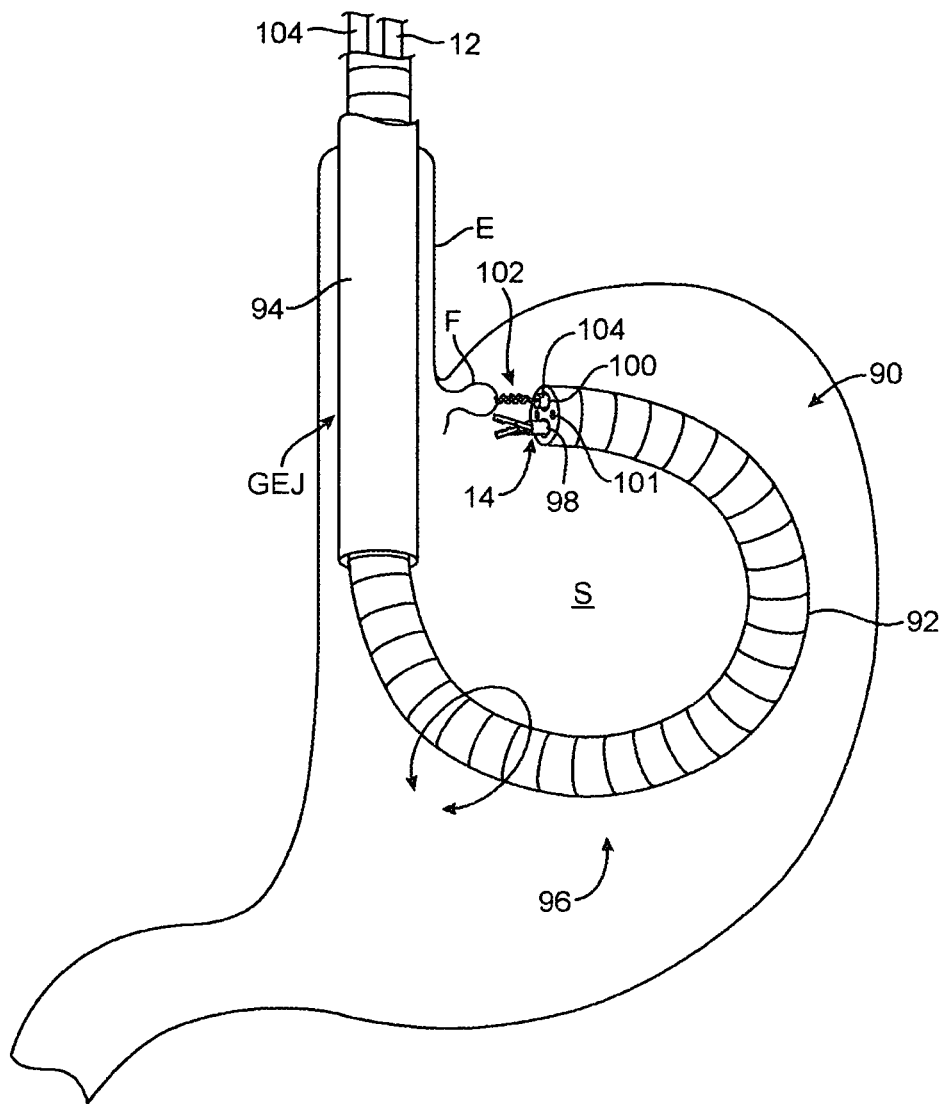
FIG. 6 illustrates one example in which a shape-lockable endoscopic assembly may be advanced into a patient's stomach per-orally and through the esophagus with a tissue manipulation assembly advanced through a first lumen and a tissue engagement member advanced through a second lumen.

As illustrated in FIG. 6, one such example is shown in which a shape-lockable endoscopic assembly 90 may be advanced into a patient's stomach S per-orally and through the esophagus E. Such an endoscopic assembly 90 may generally comprise an endoscopic device which may have a distal portion which may be articulated and steered to position its distal end anywhere within the stomach S. Once desirably configured, assembly 90 may then be locked or rigidized to maintain its shape or configuration to allow for procedures to be performed on the tissue utilizing any number of tools delivered through the assembly 90. Shape-lockable assembly 90 and its variations are described in further detail in U.S. patent application Ser. No. 10/734,562 filed Dec. 12, 2003, which is incorporated herein by reference in its entirety.

Shape-lockable assembly 90 may be generally comprised of shape-lockable endoscopic body 92 having an articulatable distal portion 96. The endoscopic body 92 may define at least first and second lumens 98, 100, respectively, through the endoscopic body 92 through which one or more tools may be deployed into the stomach S. Additional lumens may be provided through shape-lockable endoscopic body 92, such as a visualization lumen 101, through which an endoscope may be positioned to provide visualization of the region of tissue. Alternatively, an imager such as a CCD imager or optical fibers may be provided in lumen 101 to provide visualization. An optional thin wall sheath 94 may be disposed through the patient's mouth, esophagus E, and possibly past the gastroesophageal junction GEJ into the stomach S. Shape-lockable body 92 may be advanced through esophagus E (and through sheath 94, if utilized) and into stomach S while disposed in a flexible state.

Distal steerable portion 96 of endoscopic body 92 may be then articulated to an orientation, e.g., whereby distal portion 96 facilitates engagement of tissue near and/or inferior to the patient's gastroesophageal junction GEJ. Accordingly, distal steerable portion 96 may comprise a number of steering features, as described in further detail in U.S. patent application Ser. No. 10/734,562, incorporated above. With distal steerable portion 96 disposed in a desired configuration or orientation, endoscopic body 92 may be reversibly shape-locked to a rigid state such that the endoscopic body 92 maintains its position within the stomach S. Various methods and apparatus for rigidizing endoscopic body 92 along its length are also described in further detail in U.S. patent application Ser. No. 10/734,562, incorporated above.

FIG. 6 shows tissue manipulation assembly 14 having been advanced through first lumen 98 and a tissue engagement member 102 positioned upon flexible shaft 104 advanced through second lumen 100. As the tissue wall of a body lumen, such as the stomach, typically comprises an inner mucosal layer, connective tissue, the muscularis layer and the serosa layer. To obtain a durable purchase, e.g., in performing a stomach reduction procedure, tissue engagement member 102 may be advanced into contact with the tissue and preferably engages the tissue F such that when the tissue engagement member 102 is pulled proximally to draw the engaged tissue F between the jaw members 20, 22 of tissue manipulation assembly 14, at least the muscularis tissue layer and the serosa layer is drawn into tissue manipulation assembly 14.

Figure 7:
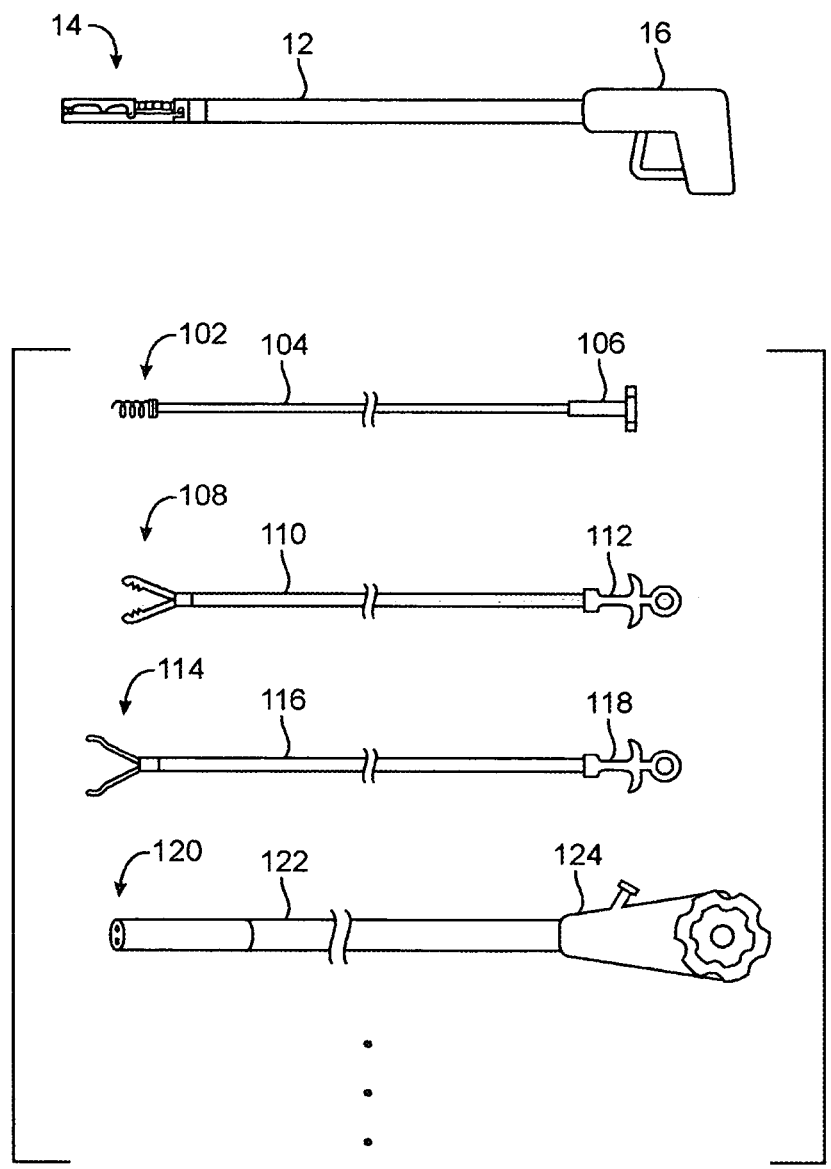
FIG. 7 illustrates a tissue manipulation assembly and examples of various tools which may be used in combination with the tissue manipulation assembly.

As tissue manipulation assembly 14 may be utilized to grasp and secure the engaged tissue, any number of tools may be utilized with tissue manipulation assembly 14, e.g., through shape-lockable endoscopic body 92, to engage and manipulate the tissue of interest relative to tissue manipulation assembly 14. FIG. 7 illustrates tissue manipulation assembly 14 upon flexible body 12 with handle 16 and examples of various tools which may be used in combination with tissue manipulation assembly 14.

Turning to FIG. 7, one example of a tool utilizable in combination with tissue manipulation assembly 14 is shown in tissue engagement member 102 as a tissue piercing helix or corkscrew structure upon flexible shaft 104 (as shown in FIG. 6). Tissue engagement member 102 may be rotated about its longitudinal axis to engage the tissue of interest by rotating handle 106 located on the proximal end of flexible shaft 104. Alternatively, a tool having aggressive tissue graspers 108 positioned upon flexible shaft 110 and articulatable via handle 112 may be utilized in combination with tissue manipulation assembly 14. Another alternative tool may be tissue graspers 114 positioned upon flexible shaft 116 and articulatable via handle 118. Tissue graspers 114 may have atraumatic grasping surfaces. In yet another alternative, an endoscope 122 having optical fibers or imager 120 may be utilized for providing visualization. Endoscope 122 may be articulated via handle 124 at its proximal end.

The examples of the various tools as shown and described are intended merely to be illustrative of the range of tools which may be usable with assembly 14 and are not intended to be limiting in any manner. Any number of other tools may be accordingly utilized and are intended to be within the scope of this disclosure.

Figure 8A:
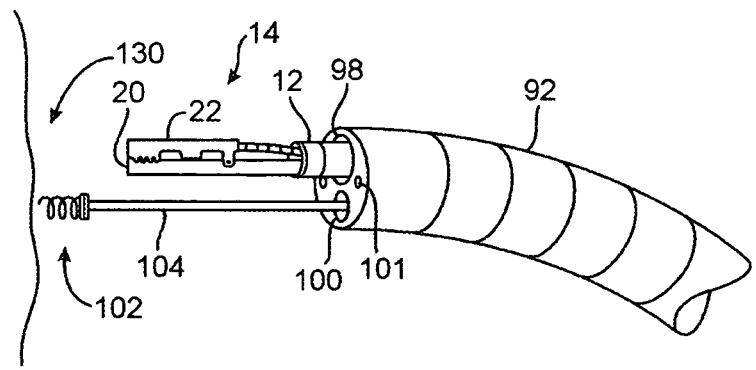

An example of performing an endoluminal tissue manipulation and securement procedure utilizing tissue manipulation assembly 14 in combination with a separate tissue grasping tool within, e.g., a patient's stomach, is illustrated in FIGS. 8A to 8D. As shown in FIG. 8A, once shape-lockable endoscopic body 92 has been introduced into the patient, e.g., trans-orally, trans-anally, percutaneously, etc., and desirably positioned relative to a tissue region of interest 130, endoscopic body 92 may be rigidized to maintain its configuration within the patient body. Alternatively, it may be left in a flexible state during the procedure.

Figure 8B:
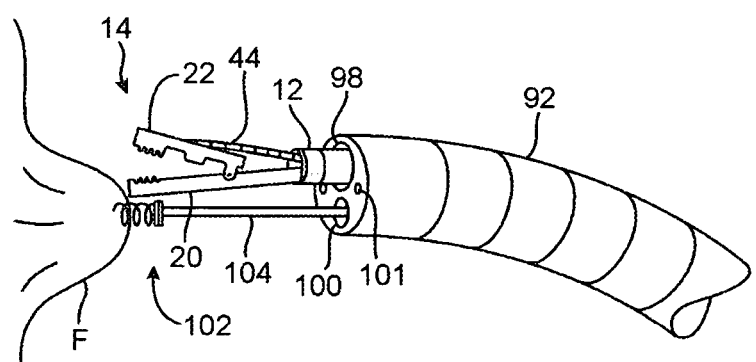

The tissue region of interest 130 as well as the procedure may be visualized through visualization lumen 101 or a separate imager, as described above. In either case, tissue manipulation assembly 14 and tissue engagement member 102 may be advanced distally out from endoscopic body 92 through their respective lumens 98, 100. Tissue engagement member 102 may be advanced into contact against the tissue surface, as shown in FIG. 8A, and then rotated via its proximal handle until the tissue is engaged. The engaged tissue F may be pulled proximally relative to endoscopic body 92 and tissue manipulation assembly 14 may be actuated via its proximally located handle into an open expanded jaw configuration for receiving the engaged tissue F, as shown in FIG. 8B.

Alternatively, once the tissue F has been engaged, tissue manipulation assembly 14 may be advanced distally in its open configuration onto the engaged tissue. In yet another variation, tissue engagement member 102 may be omitted entirely and tissue manipulation assembly 14 may be utilized alone to grasp onto the tissue region of interest 130. In yet another alternative, a second tissue manipulation assembly may be used in combination with tissue manipulation assembly 14.

Figure 8C:
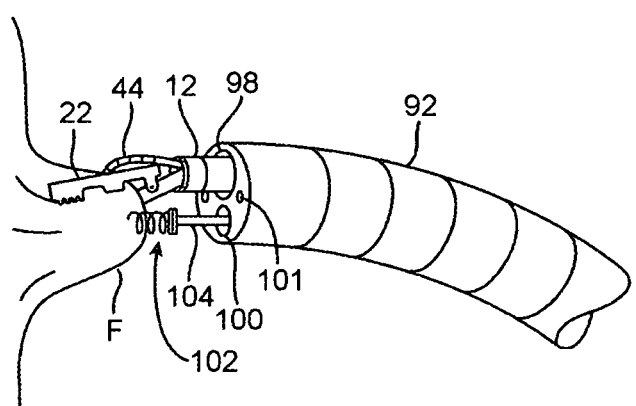

Turning back to FIG. 8B, tissue manipulation assembly 14 may be articulated to receive the engaged tissue F. As shown in FIG. 8C, once engaged tissue F is positioned between jaw members 20, 22, the launch tube may be urged proximally to actuate upper jaw member 22 to grasp or clamp upon the tissue F. Tissue engagement member 102 may be retracted from the tissue F or it may be left within the tissue while tissue manipulation assembly engages and secures the tissue F.

FIG. 8D shows a partial cross-sectional view of the tissue F while engaged to tissue manipulation assembly 14. Tissue engagement member 102 has been omitted from this view only for the sake of clarity. As mentioned above, member 102 may be left remaining in the tissue F, disengaged from tissue F, or disengaged and removed entirely from endoscopic body 92, if so desired, and another tool may be advanced through lumen 100 to facilitate the procedure. Once jaw members 20, 22 have been actuated to clamp or grasp upon tissue F by the launch tube, the launch tube may be automatically positioned into its anchor deployment configuration. The needle assembly may then be urged via manipulation from its proximal end at handle 16 through the launch tube to pierce preferably through a dual serosa layer through engaged tissue F and past lower jaw member 20. As described above, the engaged tissue F positioned between the jaw members 20, 22 is desirably engaged such that the needle body 72, when urged through the tissue F, is disposed through the muscularis and/or serosa layers of the engaged tissue F. Once needle body 72 has passed through tissue F, one or more expandable tissue anchors may be ejected from needle body 72 through needle opening 74.

Because needle body 72 may penetrate the tissue wall twice, it exits within the body lumen if utilized within, e.g., the stomach, thus reducing the potential for injury to surrounding organs. As described above, needle body 72 may define needle lumen or opening 74 through which an expandable anchor, e.g., distal anchor 82 and/or proximal anchor 84, may be situated during deployment and positioning of the assembly. A single suture or flexible element 132 (or multiple suture elements) may connect distal anchor 82 and proximal anchor 84 to one another and end in terminal loop 134. For instance, element 132 may comprise various materials such as monofilament, multifilament, or any other conventional suture material, elastic or elastomeric materials, e.g., rubber, etc.

Once distal anchor 82 has been ejected, needle body 72 may be urged proximally back through tissue F, where proximal anchor 84 may then be ejected from needle body 72 with suture 132 still connecting the two anchors 82, 84 through tissue F. Alternatively, tissue manipulation assembly 14, with suture 132 still depending therefrom, may be disengaged from tissue F and the procedure may be repeated at a second region of tissue where proximal anchor 84 may then be ejected.

FIG. 9A shows one variation where a single fold F may be secured between proximal anchor 82 and distal anchor 84. With both anchors 82, 84 disposed externally of the launch tube and suture 132 connecting the two, proximal anchor 84 may be urged into contact against tissue F. As the anchors are urged against tissue fold F, distal anchor 82 or a portion of suture 132 may be configured to provide any number of directionally translatable locking mechanisms 136 which provide for movement of an anchor along suture 132 in a first direction and preferably locks, inhibits, or prevents the reverse movement of the anchor back along suture 132.

FIG. 9B shows another variation where a at least two folds $F_1$ and $F_2$ may be secured between proximal anchor 82 and distal anchor 84. After the anchors have been ejected from needle body 72, the anchors may be approximated towards one another over suture 132 thus bringing folds $F_1$ and $F_2$ towards one another. Although a single tissue fold and a dual fold are shown in these examples, any number of folds or tissue ridges may be created using the tools disclosed herein. Moreover, these examples are merely intended to be illustrative and not limiting in any way. In either case, it may be generally desirable to form the tissue folds such that serosa-to-serosa contact 138 occurs between the layers of secured tissue, although this may not be necessary.

Various examples of cinching devices and methods which may be utilized with the tools and devices herein are described in further detail in U.S. patent application Ser. No. 10/840,950 filed May 7, 2004, which has been incorporated herein above.

Figure 10A:
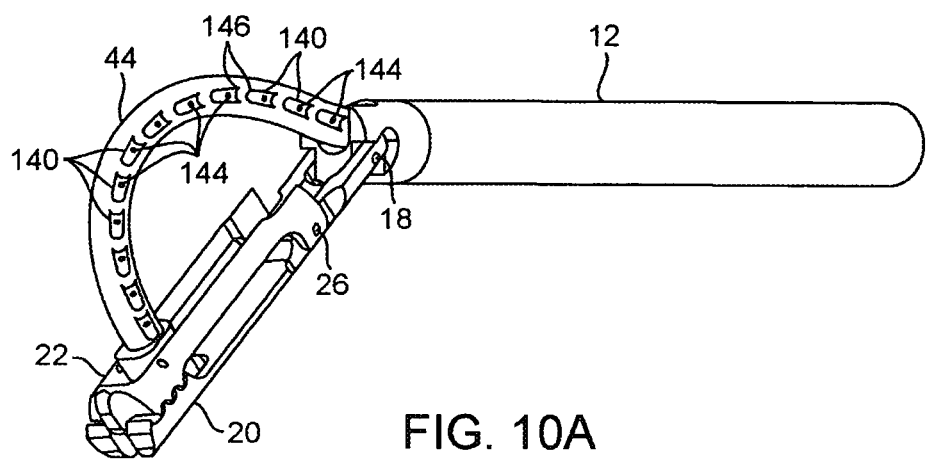
FIGS. 10A and 10B illustrate a variation of the tissue manipulation assembly in a perspective and cross-sectional view, respectively, where a number of reinforcement members or bars may be positioned along the launch tube to increase its column strength.
Figure 10B:
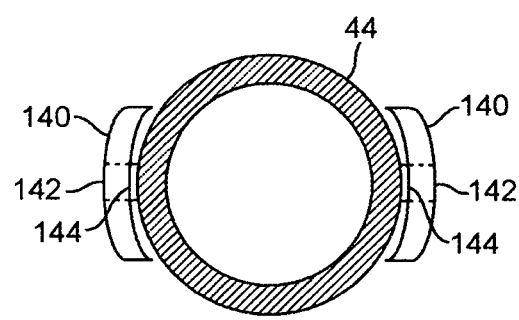

In using the launch tube as a jaw actuation mechanism, other variations of the launch tube may be utilized to ensure sufficient strength and force transmission in tissue manipulation assembly 14 for jaw member actuation. One such example is shown in the perspective view of FIG. 10A, which shows launch tube 44 having a number of reinforcement members or bars 140 aligned along one or both sides of the launch tube to provide for additional column strength. Each of the reinforcement members 140 may be pivotally attached to launch tube 44 via pivot members 144 rotatably secured within pivot channels 142, as seen in the launch tube cross-section in FIG. 10B. Moreover, each of the pivot members 144 may define cooperating adjacent members relative to one another while maintaining contact to allow for the transmission of force between the members 144. Pivot members 144 may be positioned along the length of the exposed launch tube or a portion of the launch tube; moreover, a single side of the launch tube may have pivot members 144 attached thereto. Alternatively, rather than utilizing pivot members, portions of the launch tube itself may be simply thickened to increase its column strength and force transmission capabilities.

Figure 11A:
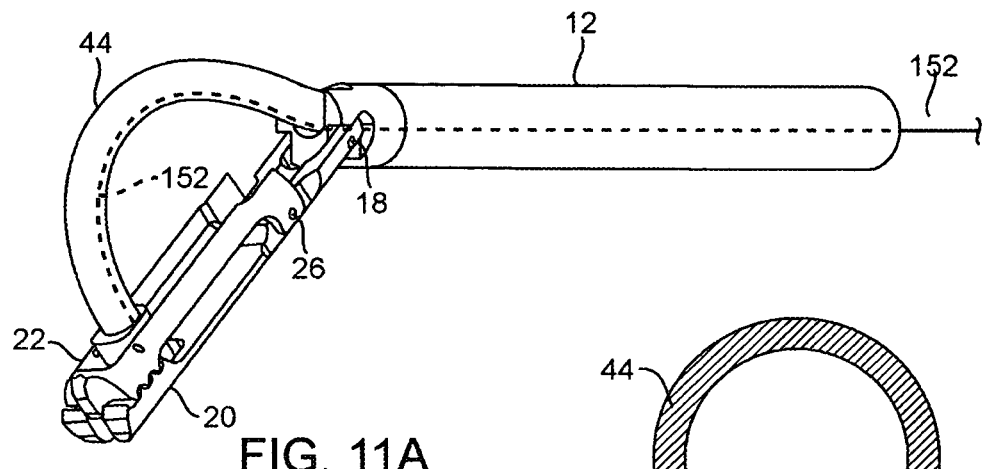
FIGS. 11A and 11B illustrate another variation of the tissue manipulation assembly in a perspective and cross-sectional view, respectively, where a pull wire may be routed through the launch tube to facilitate articulation of the launch tube and/or jaw assembly.
Figure 11B:
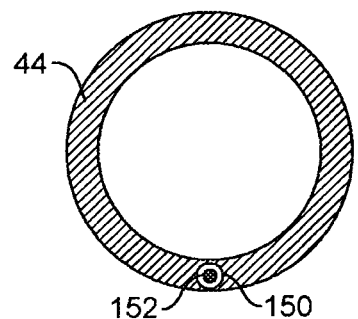
Figure 12:
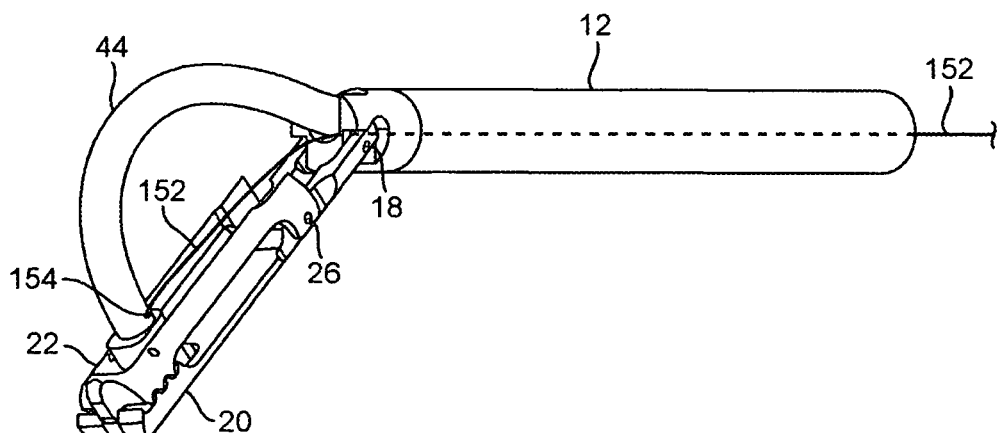
FIG. 12 illustrates yet another variation of the tissue manipulation assembly which may also utilize a pull wire connected directly to the launch tube.

In another variation, as shown in FIG. 11A and the launch tube cross-section in FIG. 11B, a pull wire 152 may be routed through tubular body 12 and launch tube 44 through a pull wire lumen 150 to provide a launch tube and jaw actuation mechanism separate from the launch tube actuation itself. Pull wire 152 may be manipulated via its proximal end at handle 16 by pulling or pushing pull wire 152 to actuate launch tube 44 and/or jaw members 20, 22. Alternatively, as seen in FIG. 12, pull wire 152 may be routed through tubular body 12 and connected directly to launch tube 44 at pull wire attachment point 154 rather than routing it through the launch tube. Again, manipulation of pull wire 152 may be utilized to articulate the launch tube configuration as well as jaw member articulation.

Referring now to FIGS. 13 and 14, a variation of the anchor assembly and the needle deployment assembly is described. As with previously described needle deployment assembly 60, assembly 60' comprises needle assembly control or housing 62, tubular sheath 64 and needle assembly 66 having needle body 72 with opening 74. Elongate pusher 76 is configured for translation within sheath 64 via actuation member 78. Pusher 76 illustratively comprises a hypotube having lumen 77 defined therethrough.

In the variation of FIGS. 13 and 14, locking mechanism 136 of anchor assembly 68' is disposed proximal of proximal anchor 84, and the anchor assembly is positioned within the distal portion of tubular sheath 64, such that the distal region of pusher 76 abuts locking mechanism 136. Suture or flexible element 132' comprising distal knot or protrusion 133 extends proximally from the knot in a manner that connects distal anchor 82, proximal anchor 84 and locking mechanism 136. Element 132' then further extends through lumen 77 of pusher 76 to a proximal region of assembly 60' such that element 132' may be manipulated by a medical practitioner from outside a patient. The medical practitioner may, for example, engage previously described suture loop 134, or may engage some other control element 134', such as a ring or handle, disposed at the proximal end of suture element 132'. As will be apparent, in another variation, element 132' may extend to the proximal region of assembly 60' alongside pusher 76 rather than within a lumen of the pusher.

With reference to FIGS. 15, a method of using anchor assembly 68' and needle deployment assembly 60' is described. For the purposes of illustration, the assemblies are shown securing tissue without use of a tissue manipulation assembly. However, it should be understood that the assemblies alternatively may be used in combination with a tissue manipulation assembly, such as previously described tissue manipulation assembly 14 of assembly 10.

In FIG. 15A, needle deployment assembly 60' has been positioned in proximity to approximated tissue T. The assembly is advanced such that needle assembly 66 pierces the tissue and is advanced through and across the tissue, as in FIG. 15B. Pusher 76 is advanced within the lumen of sheath 64 via actuation member 78, such that distal anchor 82 of anchor assembly 68' is ejected through opening 74 of needle body 72 of needle assembly 66 on the distal side of approximated tissue T. Needle deployment assembly 60' and pusher 76 then are retracted such that the pusher and needle assembly 66 again are disposed on the proximal side of the approximated tissue, as in FIG. 15C. Next, pusher 76 is distally advanced relative to sheath 64 to eject proximal anchor 84 from the sheath.

Figure 15D:
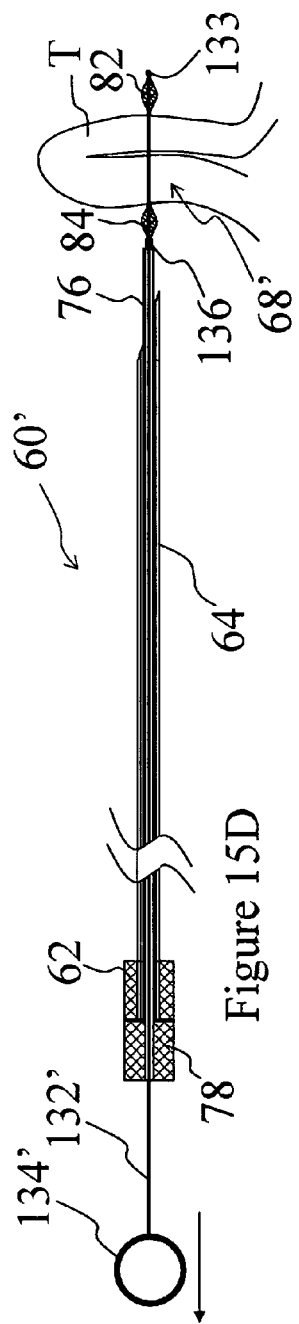

In FIG. 15D, with the proximal and distal anchors of anchor assembly 68' disposed 25 on either side of the approximated tissue, the anchor assembly is cinched by retracting control element 134' relative to needle deployment assembly 60'. Pusher 76 abuts locking mechanism 136 and urges it distally during proximal retraction of element 134', which shortens the length of suture element 132' disposed between distal anchor 82 and proximal anchor 84, thereby cinching anchor assembly 68'. Locking mechanism 136 ensures that the 30 anchors remain cinched by resisting distal passage of element 132' through the mechanism, thereby resisting subsequent separation of the proximal and distal anchors.

Figure 15E:
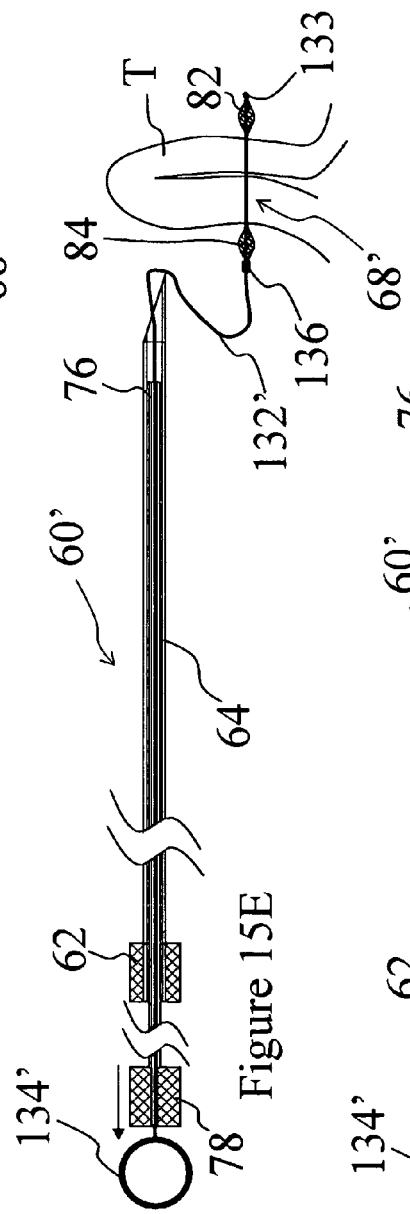
Figure 15F:
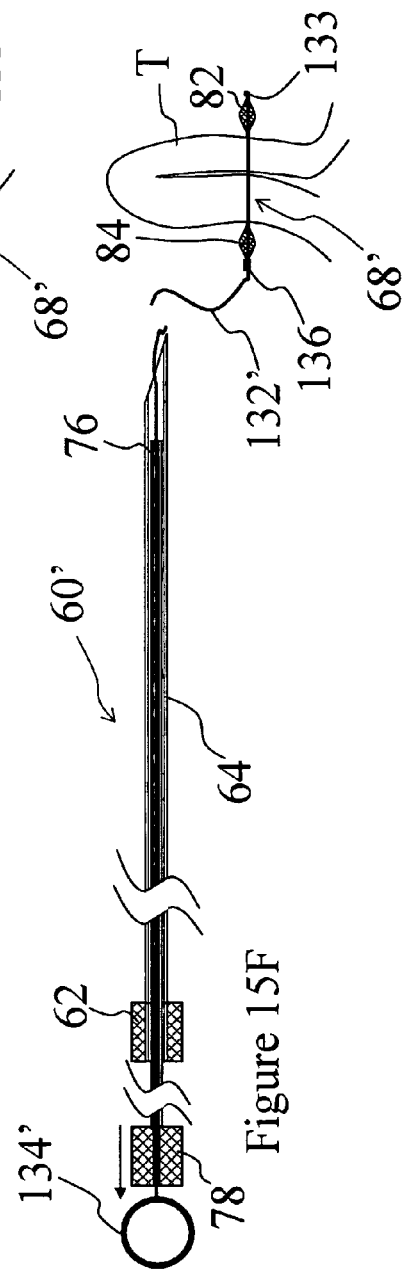

With anchor assembly 68' cinched, pusher 76 is retracted relative to sheath 64 such that needle assembly 66 engages suture element 132', as in FIG. 15E. The needle assembly cuts the suture proximal of locking mechanism 136, as in FIG. 15F. The medical practitioner may facilitate cutting of the suture element by manipulating control element 134' of anchor assembly 68' and/or by manipulating needle assembly control 62 of needle deployment assembly 60'.

Referring now to FIG. 16, a variation of the suture element of anchor assembly 68' is described. In FIG. 16, suture element 132" comprises segment 135 of reduced integrity. The segment may for example, comprise fewer suture strands or may be reduced in integrity via chemical, electrical, thermal or physical processing, etc. Segment 135 may locally reduce the tensile strength of element 132" to a desired threshold. When used to cinch anchor assembly 68' in combination with anchor deployment assembly 60', the segment may obviate a need to cut the suture with needle assembly 66 after cinching of the anchor assembly. Specifically, the anchor assembly may be cinched to a desired tension after which segment 135 plastically deforms and snaps, leaving the anchor assembly cinched and in place.

With reference to FIG. 17, a variation of the needle assembly of needle deployment assembly 60' is described. Needle body 72' of needle assembly 66' may comprise one or more recessed cut-outs 73 having sharpened edges E for cutting the suture element. After cinching of anchor assembly 68', the suture element may be snagged within a cut-out 73 and cut by the sharpened edge of the cut-out.

Referring now to FIG. 18, alternative control mechanisms for needle deployment assembly 60' are described. Actuation member 78' for controlling pusher 76 may be integrated with needle assembly control 62', such that the actuation member is advanceable in controlled increments relative to the needle assembly control via detents 63 of the needle assembly control that coact with actuation member 78'.

With reference to FIGS. 19, another variation of the anchor assembly and needle deployment assembly is shown. Control element 134' of anchor assembly 68' is coupled to or abuts needle assembly control 62' of needle deployment assembly 60'. When distal anchor 82 of anchor assembly 68' is disposed on the distal side of approximated tissue T, as in FIG. 19A, the proximal and distal ends of suture element 132' are constrained. Thus, as seen in FIGS. 19A and 19B, advancement of pusher 76 via actuation member 78' advances both proximal anchor 84 and locking mechanism 136 of anchor assembly 68'. This causes the anchor assembly to be progressively cinched as the proximal anchor is advanced. Once the anchor assembly has been ejected from sheath 64, as in FIG. 19B, and adequately cinched, as in FIG. 19C, suture element 132' may be cut proximal of the locking mechanism, e.g., with needle assembly 66 as described previously.

Figure 20A:
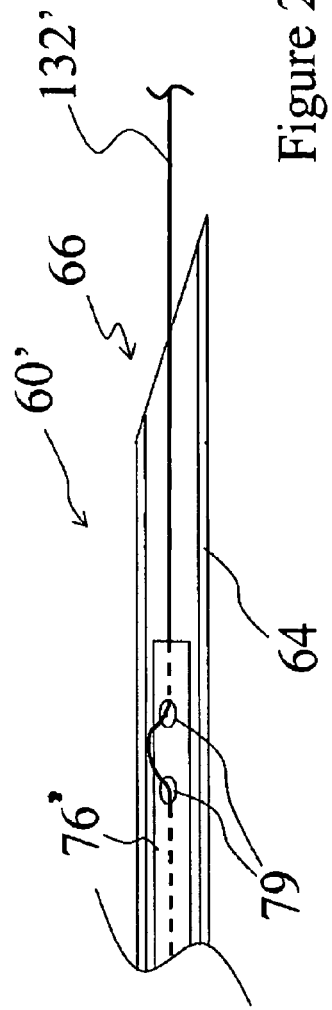
FIGS. 20A to 20C are schematic views illustrating another variation of the needle deployment assembly.
Figure 20B:
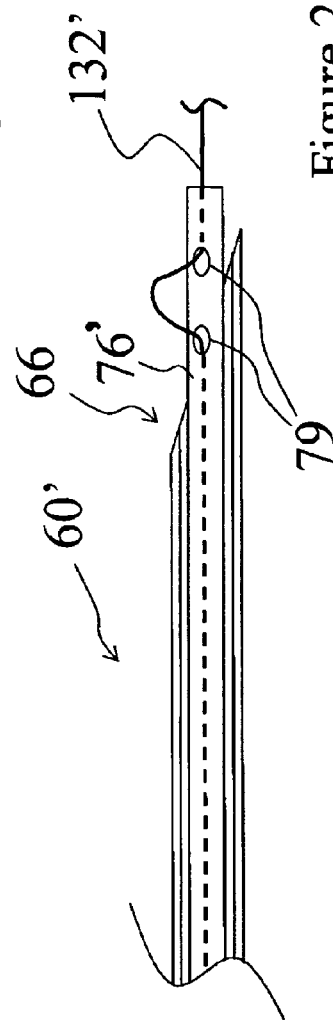
Figure 20C:
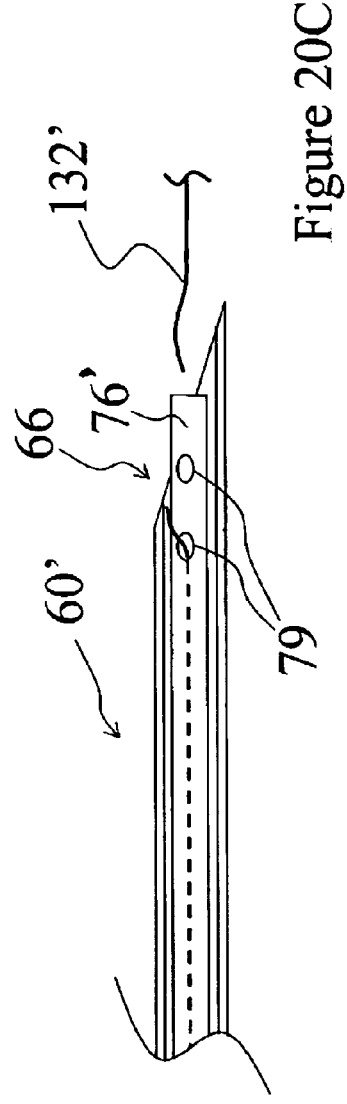

Referring to FIGS. 20, a variation of the needle deployment assembly is described. Pusher 76' comprises suture ports 79 through which suture element 132 of anchor assembly 68' is routed. As seen in FIG. 20A, with pusher 76' disposed within tubular sheath 64 of needle deployment assembly 60', suture element 132' passes out of the pusher between the suture ports and is disposed between the pusher and the interior wall of the tubular sheath. As seen in FIG. 20B, when pusher 76' is advanced through and distal of needle assembly 66, e.g., to eject proximal anchor 84 of anchor assembly 68' from the needle deployment assembly and/or to cinch the anchor assembly, the section of suture element 132' between the suture ports is exposed. Subsequent retraction of the pusher relative to the needle assembly causes the section of exposed suture to contact the sharpened edge of needle assembly 66, thereby severing suture element 132' as in FIG. 20C.

Turning now to FIGS. 21, another variation of the needle deployment assembly is shown. In this variation, suture element 132''' may form a terminal loop 158 through which a release suture or wire 156 may be passed. Release suture or wire 156 may be routed through the length of the needle deployment assembly and through pusher 76, as described above, and both release suture or wire 156 and terminal loop 158 may both be situated within pusher 76, as shown in FIG. 21A. After deployment of the anchors into tissue and cinching of the assembly, as described above, one end of release suture or wire 76 may be pulled or tensioned proximally in the direction shown by arrow 162, as in FIG. 21B. This pulling may draw a terminal end of release suture or wire 156 through pusher 76 until terminal loop 158 of suture element 132''' has been released therefrom, as shown in FIG. 21C.

In yet another variation shown in FIG. 22A, terminal loop 158 of suture element 132''' may be seen restrained within pusher 76 via reconfigurable hook 164 of release wire 156'. Here, release wire 156' may be fabricated from a shape memory or superelastic alloy material, such as Nitinol, which has been preformed to reconfigure its terminal end from a hook 164 configuration to a straightened or opened configuration once released from the constraints of pusher 76. Thus, after deployment and cinching of the anchor assembly, release wire 156' may be advanced distally through pusher 76, as shown in FIG. 22B, until reconfigurable hook 164, which is retained in a hooked or obstructive configuration within the lumen of pusher 76, has been advanced out of pusher 76. Once free from the constraints of the lumen, hook 164 may reconfigure itself into an opened or straightened configuration to thereby release terminal loop 158 of suture element 132''', as shown in FIG. 22C. Hook 164 having released terminal loop 158, may then be withdrawn proximally back into pusher 76 in its straightened configuration.

In another variation shown in FIG. 23A, a terminal end of suture element 132''' may have an obstructive or enlarged element 160, e.g., a knot, formed thereon. The terminal end of suture element 132''' with obstructive element 160 may be looped around release suture or wire 156 and retained within the lumen of pusher 76. After anchor deployment and cinching, release suture or wire 156 may be drawn distally with looped obstructive element 160 retained securely thereto, as shown in FIG. 23B, until obstructive element 160 and release suture or wire 156 have been advanced out of pusher 76. Once free from the constraints of the pusher lumen, obstructive element 160 may be released from release suture or wire 156, as shown in FIG. 23C, to thus release suture element 132'''.

Although a number of illustrative variations are described above, it will be apparent to those skilled in the art that various changes and modifications may be made thereto without departing from the scope of the invention. Moreover, although specific configurations and applications may be shown, it is intended that the various features may be utilized in various combinations and in various types of procedures as practicable. It is intended in the appended claims to cover all such changes and modifications that fall within the true spirit and scope of the invention.

What is claimed is:

1. A method of securing tissue within a hollow body organ, comprising:
- endoluminally advancing a tissue grasping tool into the hollow body organ;
- pivoting the tissue grasping tool about a fixed pivot joint connecting the grasping tool to an elongate member;
- reversibly engaging the tissue within the hollow body organ with a tissue engagement member adjacent to the tissue grasping tool;
- pulling the engaged tissue with the tissue engagement member;
- clamping the engaged tissue with the tissue grasping tool;
- after engaging the tissue and pulling the tissue, piercing through the engaged tissue with a needle of an anchor deployment assembly, the needle having a sharpened tip, with the needle separate from the tissue engagement member;
- deploying a distal tissue anchor through the needle on a distal side of the engaged tissue;
- retracting the needle to a proximal side of the engaged tissue;
- deploying a proximal tissue anchor through the needle on the proximal side of the engaged tissue, with a suture connecting the proximal and distal tissue anchors; and
- severing the suture adjacent to the proximal anchor using the sharpened tip of the needle, thereby releasing the proximal and distal anchors from the anchor deployment assembly.

2. The method of claim 1 further comprising cinching the proximal and distal anchors to secure the engaged tissue prior to severing the suture element.

3. The method of claim 1 wherein deploying the proximal and distal anchors through the needle further comprises advancing a pusher through the needle.

4. The method of claim 1 wherein endoluminally advancing comprises advancing the tissue grasping tool transesophageally into a stomach.

5. The method of claim 1 further comprising, prior to advancing the needle through the engaged tissue, positioning the anchor deployment assembly at least partially within the tissue grasping tool.

6. A method of deploying an anchor assembly, comprising:
- endoluminally advancing a tissue grasping tool of an endoscopic body into a hollow body organ;
- pivoting the tissue grasping tool about a pivot joint connecting the grasping tool to a flexible body of the tissue grasping tool;
- reversibly engaging a region of tissue within the hollow body organ with a tissue engagement member of the endoscopic body;
- pulling the engaged region of tissue with the tissue engagement member towards the endoscopic body to form a tissue fold;
- clamping the tissue fold with the tissue grasping tool while pivoting the tissue grasping tool relative to the flexible body;
- after clamping the tissue fold, piercing the tissue fold with a needle projecting out of a distal end of the flexible body and having a sharp edge;
- deploying an anchor assembly from the flexible body, the anchor assembly including a suture and a cinching member;
- advancing the cinching member over the suture; and
- severing the suture using the sharp edge of the needle.

7. The method of claim 6, wherein deploying an anchor assembly comprises deploying an anchor assembly through a needle of an anchor deployment assembly, thereby securing the region of tissue.

8. The method of claim 7, wherein severing the suture releases the tissue anchor assembly from the anchor deployment assembly.

9. The method of claim 6 wherein endoluminally advancing comprises advancing the tissue grasping tool transesophageally into a stomach.

10. The method of claim 7, further comprising positioning the anchor deployment assembly at least partially within the tissue grasping tool.

* * * * *